US008906685B2

(12) United States Patent
Takayama et al.

(10) Patent No.: US 8,906,685 B2
(45) Date of Patent: Dec. 9, 2014

(54) HANGING DROP DEVICES, SYSTEMS AND/OR METHODS

(75) Inventors: Shuichi Takayama, Ann Arbor, MI (US); Yi-Chung Tung, Ann Arbor, MI (US); Amy Yu-Ching Hsiao, Ann Arbor, MI (US); Edward Jan, Ann Arbor, MI (US)

(73) Assignees: The Regents of The University of Michigan, Ann Arbor, MI (US); 3D Biomatrix, Inc., Ann Arbor, MI (US)

( * ) Notice: Subject to any disclaimer, the term of this patent is extended or adjusted under 35 U.S.C. 154(b) by 0 days.

(21) Appl. No.: 13/575,558

(22) PCT Filed: Jan. 28, 2011

(86) PCT No.: PCT/US2011/022966
§ 371 (c)(1),
(2), (4) Date: Oct. 11, 2012

(87) PCT Pub. No.: WO2011/094572
PCT Pub. Date: Aug. 4, 2011

(65) Prior Publication Data
US 2013/0040855 A1 Feb. 14, 2013

Related U.S. Application Data

(60) Provisional application No. 61/299,011, filed on Jan. 28, 2010.

(51) Int. Cl.
*C12N 5/00* (2006.01)
*C40B 30/06* (2006.01)
*B01L 3/00* (2006.01)
*C12M 1/32* (2006.01)
*C12M 1/12* (2006.01)
*G01N 35/10* (2006.01)
*G01N 35/02* (2006.01)

(52) U.S. Cl.
CPC ............ *C12N 5/0062* (2013.01); *B01L 3/50853* (2013.01); *B01L 3/50857* (2013.01); *B01L 3/5088* (2013.01); *C12M 23/12* (2013.01); *C12M 25/01* (2013.01); *B01L 2200/025* (2013.01); *B01L 2200/141* (2013.01); *B01L 2200/142* (2013.01); *B01L 2300/0829* (2013.01); *B01L 2300/161* (2013.01); *G01N 2035/1046* (2013.01); *G01N 35/028* (2013.01)
USPC ................ 435/383; 435/395; 506/10; 506/14

(58) Field of Classification Search
None
See application file for complete search history.

(56) References Cited

U.S. PATENT DOCUMENTS 4,411,990 A 10/1983 Salmon et al.
5,023,172 A 6/1991 Djordjevic
(Continued)

FOREIGN PATENT DOCUMENTS

CN 102257123 A 11/2011
EP 1336433 A1 8/2003
(Continued)

OTHER PUBLICATIONS

Tung et al., "High-throughput 3D spheroid culture and drug testing using a 384 hanging drop array." Analyst. Feb. 7, 2011;136(3):473-8.
(Continued)

*Primary Examiner* — Betty Forman
(74) *Attorney, Agent, or Firm* — Tanya A. Arenson; Casimir Jones, S.C.

(57) ABSTRACT

The present disclosure relates general to devices, systems, and methods of using such devices in creating and handling hanging drops of fluid. The present disclosure also relates to cell culture devices, methods and/or systems of using such devices as well as the use of cell culture devices, for example, for research and high throughput screening.

10 Claims, 20 Drawing Sheets

(56) References Cited

U.S. PATENT DOCUMENTS

| | | |
|---|---|---|
| 5,229,288 A | 7/1993 | Mori et al. |
| 5,284,753 A | 2/1994 | Goodwin, Jr. et al. |
| 5,587,321 A | 12/1996 | Smith et al. |
| 5,728,541 A | 3/1998 | Kornblith |
| 5,882,930 A | 3/1999 | Baier |
| 6,004,528 A | 12/1999 | Bergstein |
| 6,110,273 A * | 8/2000 | Sanjoh .................. 117/68 |
| 6,416,967 B2 | 7/2002 | Kornblith |
| 6,632,655 B1 | 10/2003 | Mehta et al. |
| 6,716,629 B2 | 4/2004 | Hess et al. |
| 6,887,680 B2 | 5/2005 | Kornblith |
| 6,900,027 B1 | 5/2005 | Kornblith |
| 6,933,129 B1 | 8/2005 | Kornblith |
| 6,984,522 B2 | 1/2006 | Clarke et al. |
| 6,998,513 B1 | 2/2006 | Barsky et al. |
| 7,052,720 B1 | 5/2006 | Jones |
| 7,112,241 B2 | 9/2006 | Sha |
| 7,112,415 B2 | 9/2006 | Kornblith |
| 7,115,360 B2 | 10/2006 | Clarke et al. |
| 7,169,577 B2 | 1/2007 | Wang et al. |
| 7,208,125 B1 | 4/2007 | Dong |
| 7,314,731 B2 | 1/2008 | Kornblith |
| 7,534,396 B2 | 5/2009 | Knebel et al. |
| 2002/0119565 A1 | 8/2002 | Clarke et al. |
| 2002/0127149 A1 | 9/2002 | Dubrow et al. |
| 2002/0192638 A1 | 12/2002 | Kornblith |
| 2003/0235519 A1 | 12/2003 | Sha et al. |
| 2004/0023375 A1 | 2/2004 | Kornblith et al. |
| 2004/0141895 A1 | 7/2004 | Sha |
| 2004/0259177 A1 | 12/2004 | Lowery et al. |
| 2005/0118711 A1 | 6/2005 | Nordheim et al. |
| 2005/0130237 A1 | 6/2005 | Strebel et al. |
| 2005/0202410 A1 | 9/2005 | Kornblith |
| 2005/0202411 A1 | 9/2005 | Kornblith |
| 2006/0051325 A1 | 3/2006 | Clarke et al. |
| 2006/0073125 A1 | 4/2006 | Clarke |
| 2006/0078993 A1 | 4/2006 | Phan et al. |
| 2006/0083682 A1 | 4/2006 | Bergstein |
| 2006/0233809 A1 | 10/2006 | Smith et al. |
| 2007/0036800 A1 | 2/2007 | Bergstein |
| 2007/0148767 A1 | 6/2007 | Yang et al. |
| 2007/0154358 A1 | 7/2007 | Dong |
| 2007/0259969 A1 | 11/2007 | Clarke et al. |
| 2007/0292389 A1 | 12/2007 | Stassi et al. |
| 2008/0038770 A1 | 2/2008 | Hansford et al. |
| 2008/0064049 A1 | 3/2008 | Clarke et al. |
| 2008/0233607 A1 | 9/2008 | Yu et al. |
| 2011/0306122 A1 | 12/2011 | Moritz et al. |

FOREIGN PATENT DOCUMENTS

| | | |
|---|---|---|
| EP | 2189519 A1 | 5/2010 |
| WO | 03078700 A1 | 9/2003 |
| WO | 2005001072 A1 | 1/2005 |
| WO | 2005089945 A1 | 9/2005 |
| WO | 2007100870 A2 | 9/2007 |
| WO | 2008123741 A1 | 10/2008 |
| WO | 2010031194 A1 | 3/2010 |

OTHER PUBLICATIONS

Kelm et al, "Method for Generation of Homogeneous Multicellular Tumor Spheroids Applicable to a Wide Variety of Cell Types." Biotechnology and Bioengineering Jul. 20, 2003, vol. 839(2): 173-180.

Moeller et al., "A microwell array system for stem cell culture." Biomaterials 2008, 29: 752-763.

Kobel & Lutolf, "High-throughput methods to define complex stem cell niches." Biotechniques 2010, 48(4):ix-xxii.

Kalinin et al, "Controlling microdrop shape and position for biotechnology using micropatterned rings." Microfluid Nanofluid 2008, 5:449-454.

Ungrin et al, "Reproducible, Ultra High-Throughput Formation of Multicellular Organization from Single Cell Suspension—Derived Human Embryonic Stem Cell Aggregates." PLoS One 2008, 3(2):1-12.

Nanoculture Plate Offers New Solution for Drug Discovery Brochure, www.infinitebio.com, 2 pages.

Pampaloni et al., "The third dimension bridges the gap between cell culture and live tissue." Nature Reviews 2007, 8:839-845.

de Ridder et al., "Autologous spheroid culture: a screening too for human brain tumour invasion." Critical Reviews in Oncology/Hemotology 36:107-122 (2000).

* cited by examiner

Figure 2
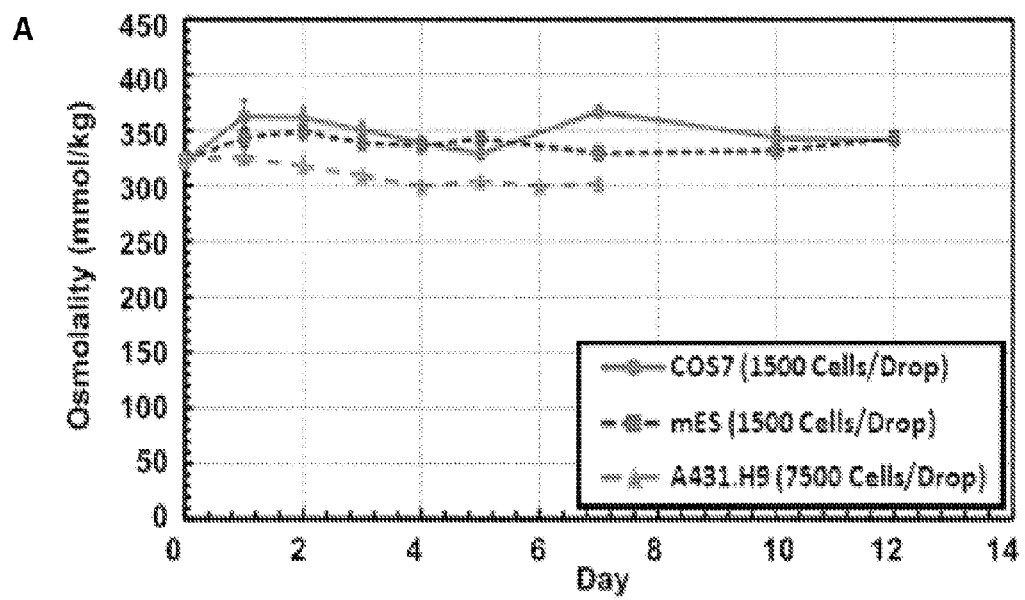
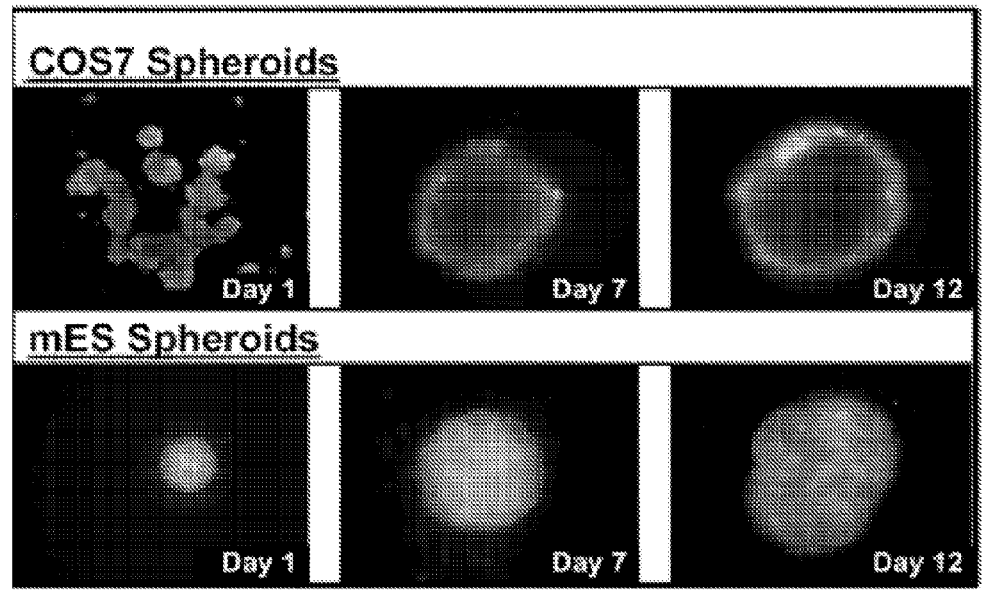

Figure 2 (cont)
C
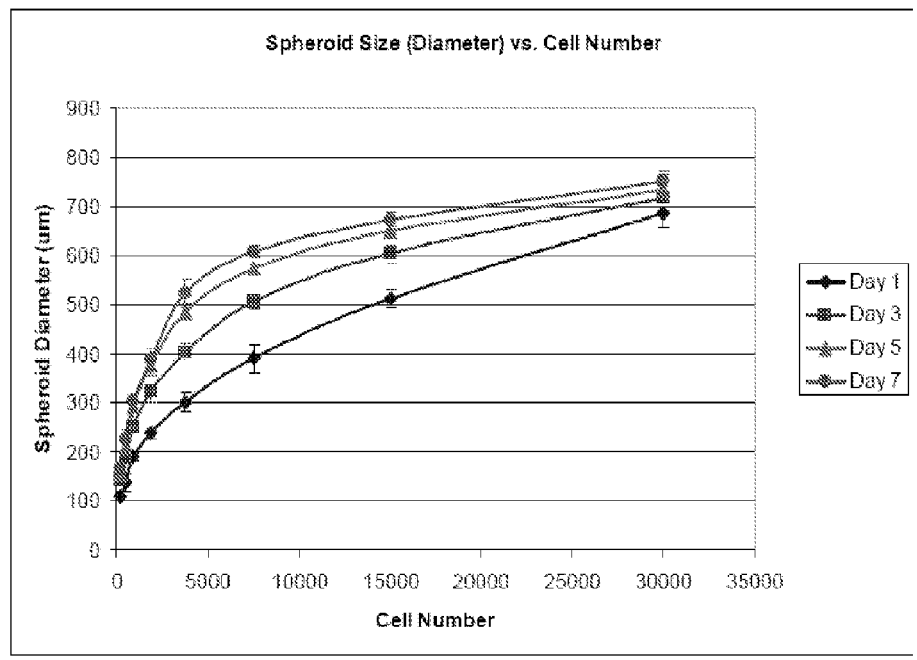
D
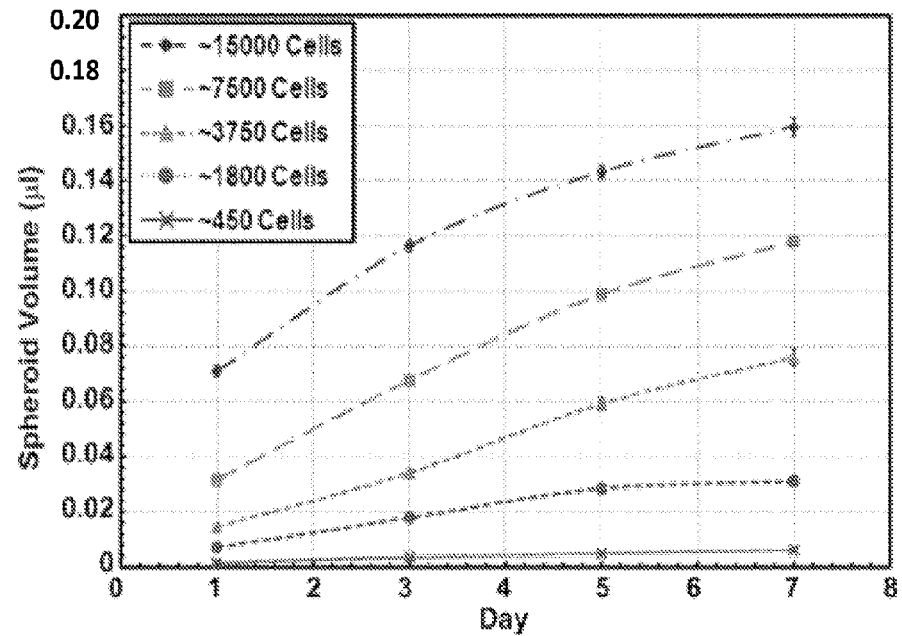

Figure 4
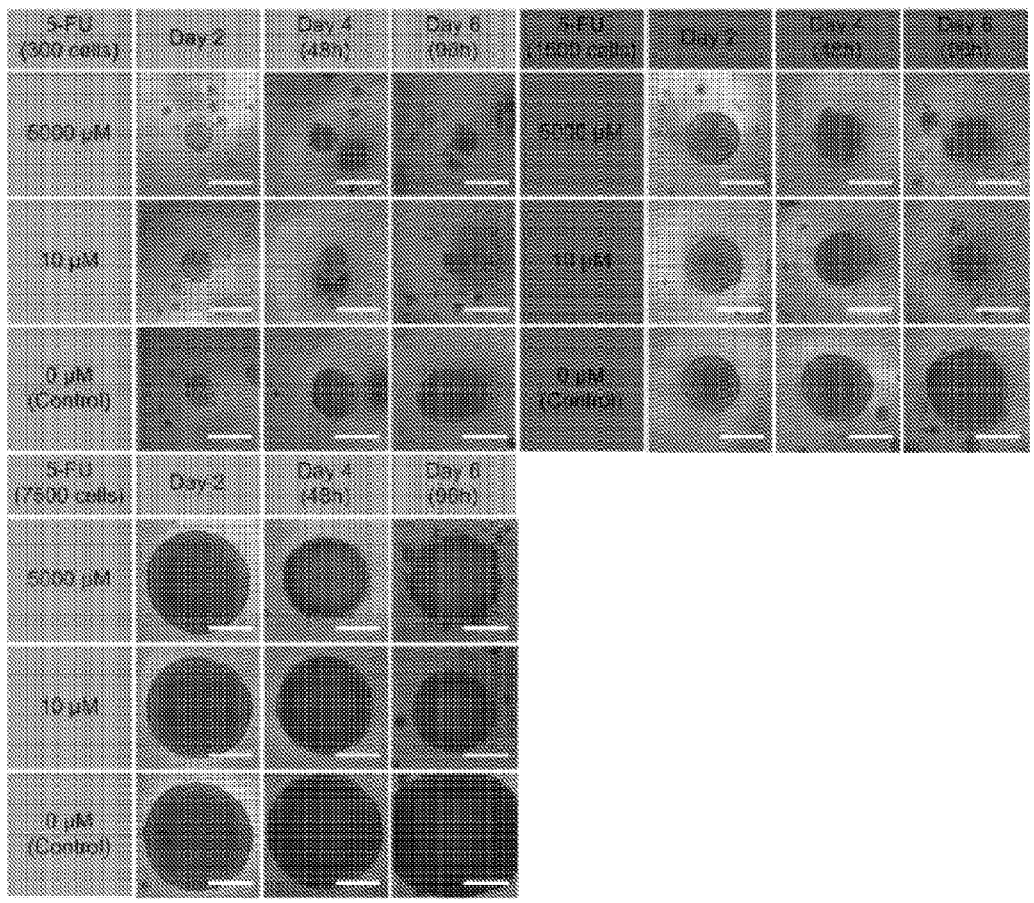
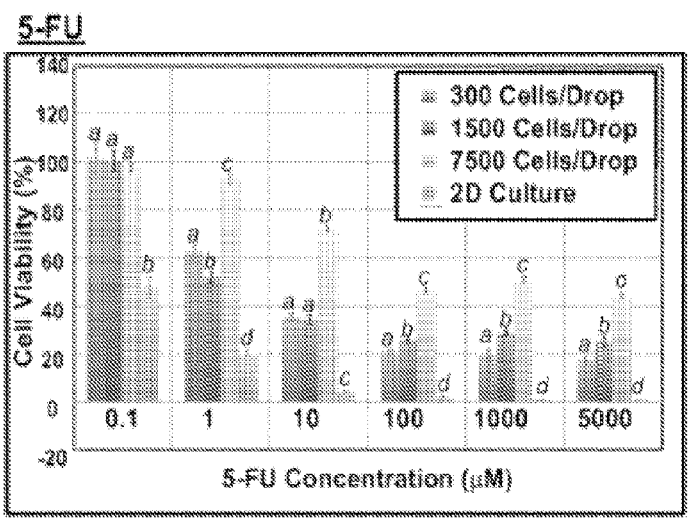

mES Spheroids

Figure 15
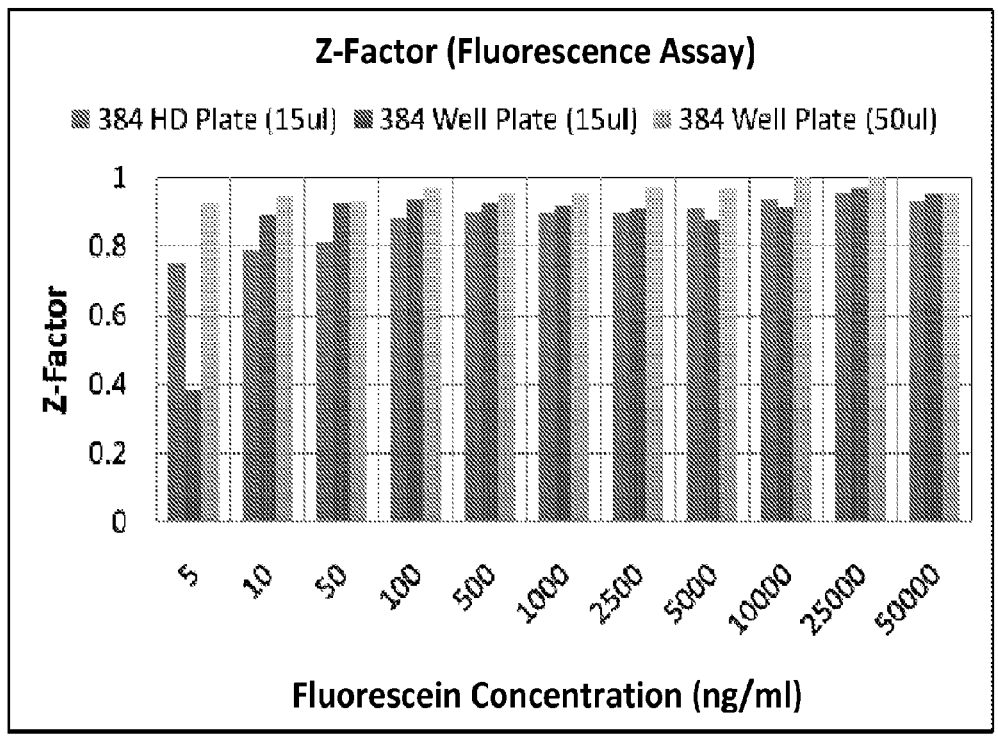
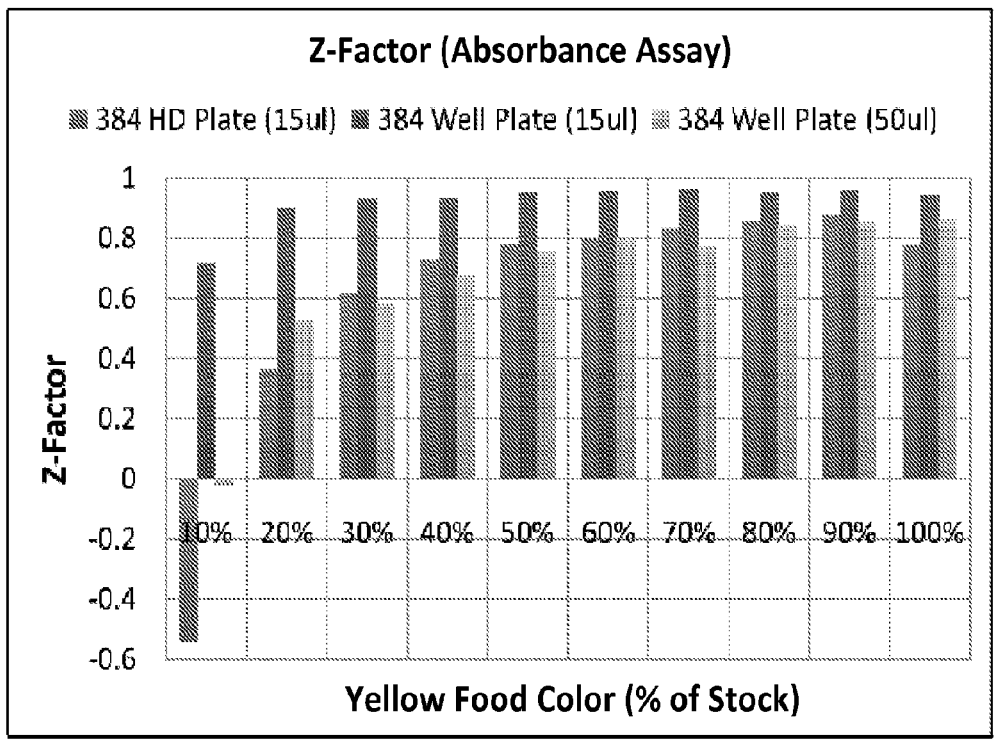

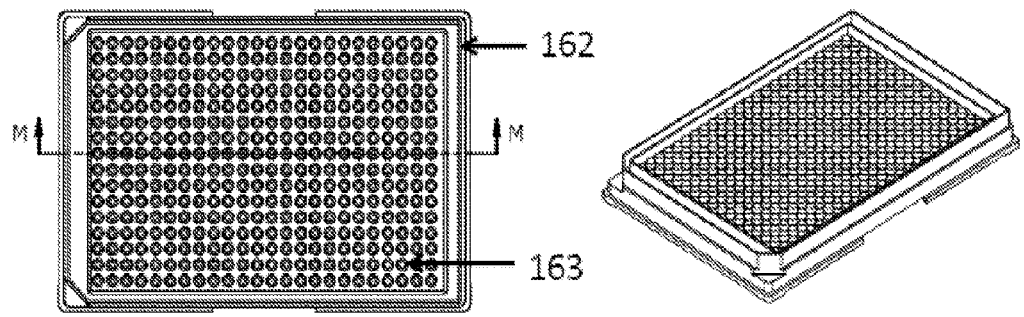
Figure 16A         Figure 16B
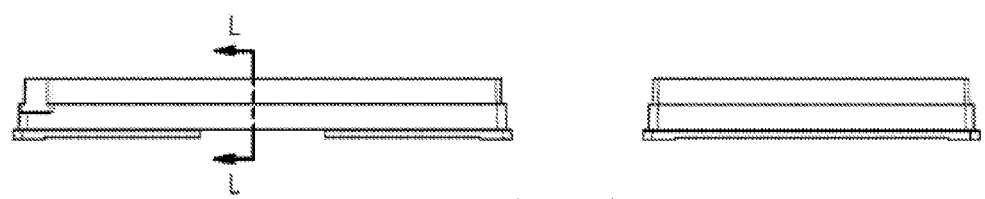
Figure 16C         Figure 16D
 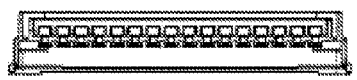
Figure 16E         Figure 16F Figure 17
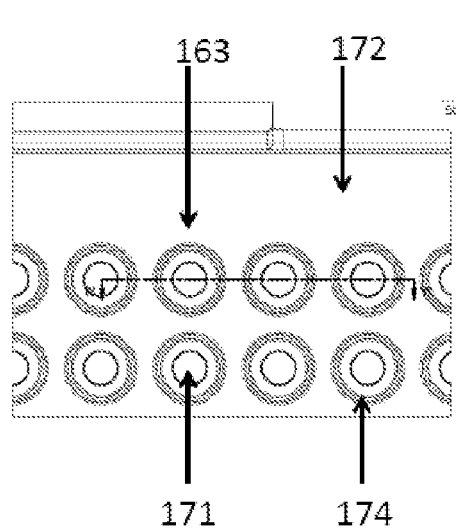
Figure 17A
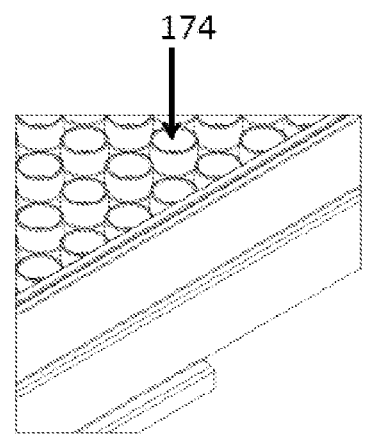
Figure 17B
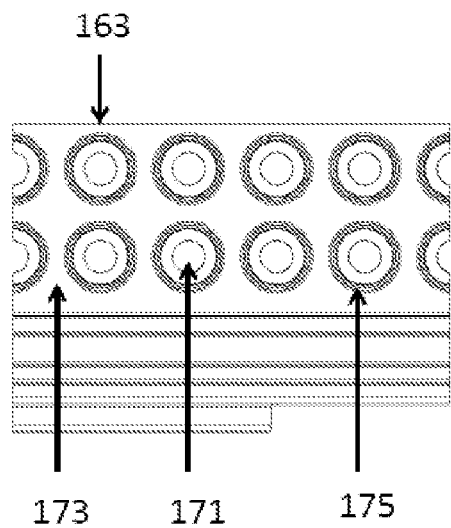
Figure 17C
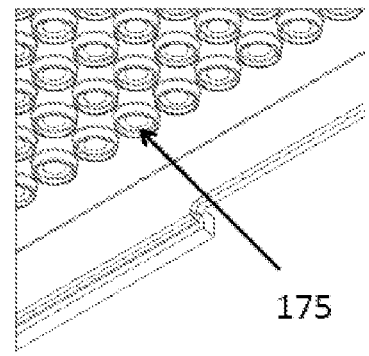
Figure 17D

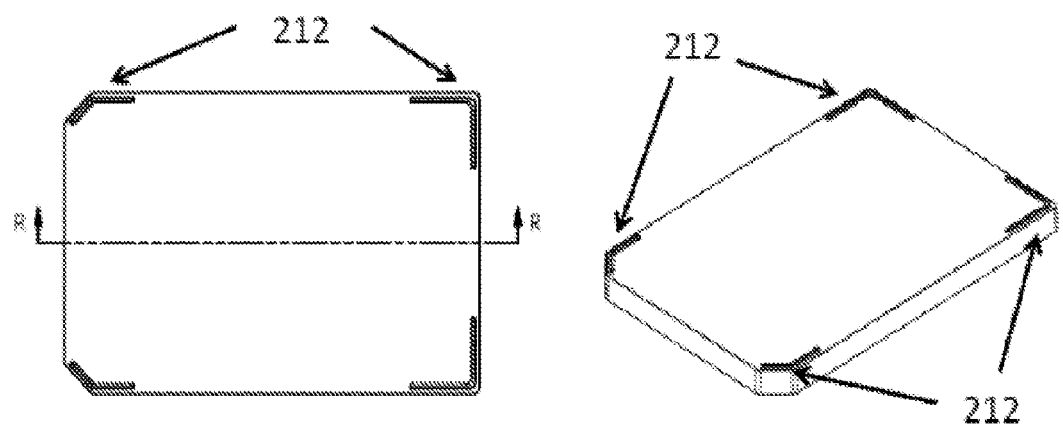
Figure 21A            Figure 21B
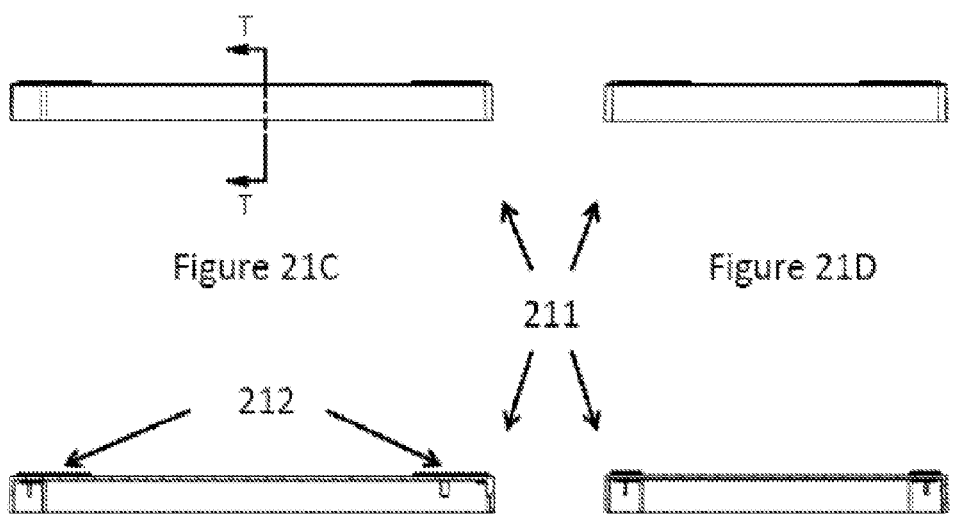
Figure 21C            Figure 21D
Figure 21E            Figure 21F

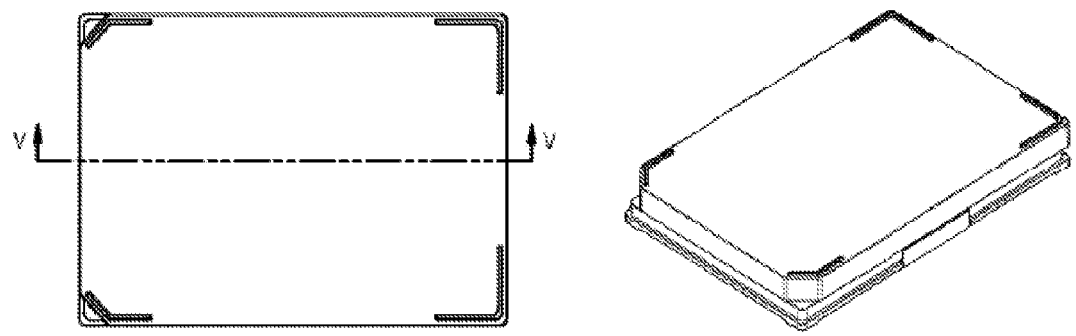
Figure 22A   Figure 22B
221
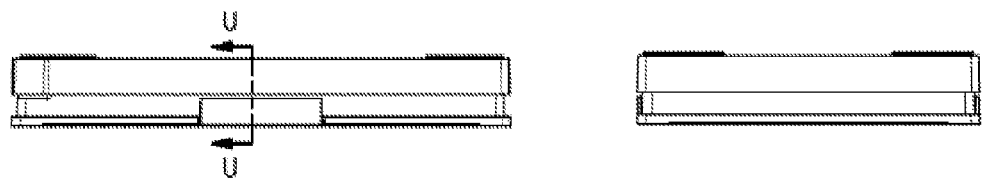
Figure 22C   Figure 22D
221
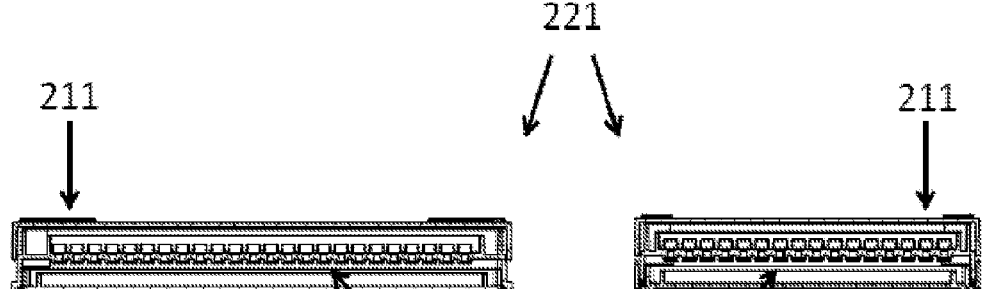
211   211
Figure 22E   201   Figure 22F
161

Figure 23
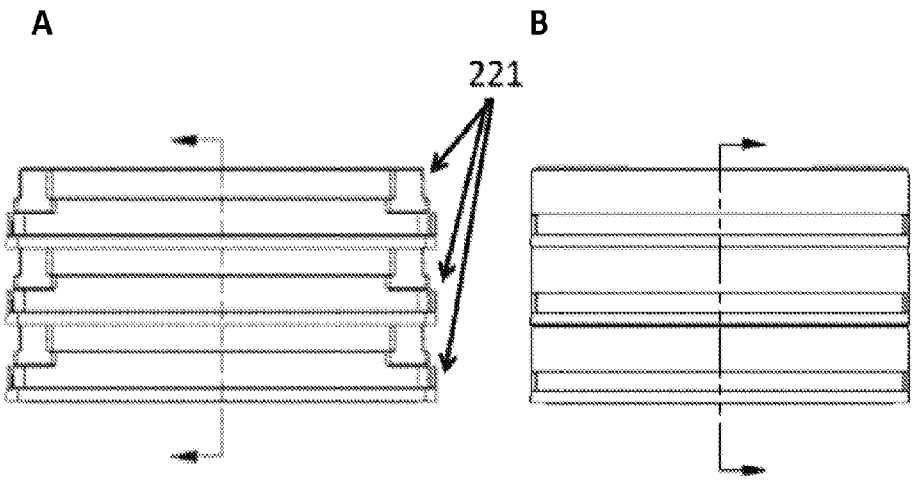
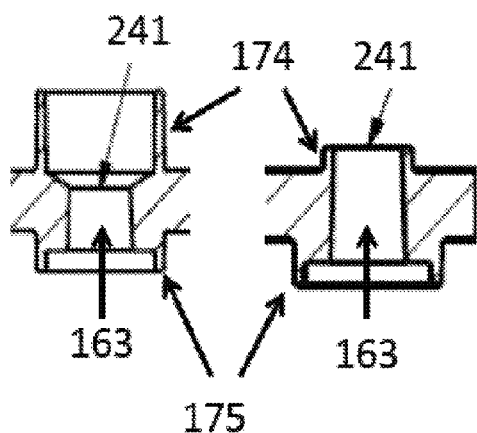
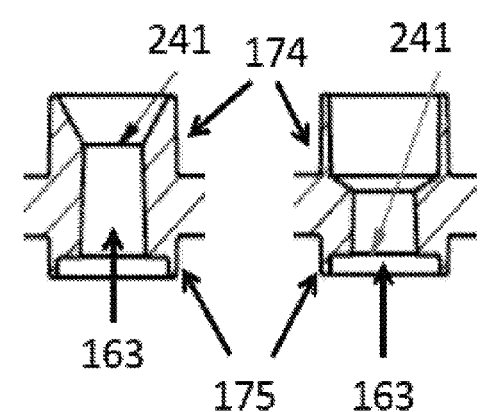
Figure 24A    Figure 24B    Figure 24C    Figure 24D

HANGING DROP DEVICES, SYSTEMS AND/OR METHODS

This application is a national phase application under 35 U.S.C. §371 of PCT International Application No. PCT/US2011/022966, filed on Jan. 28, 2011, which claims priority to U.S. provisional application 61/299,011, filed Jan. 28, 2010, each of which are herein incorporated by reference in its entirety. In addition, the following manual entitled Sambrook, J. et al., Molecular Cloning: A Laboratory Manual, 2nd ed., Cold Spring Harbor Laboratory Press, New York (1989) pp.16.9-16.15 is herein incorporated by reference in its entirety.

FIELD

The present disclosure relates generally to devices, systems, and methods of using such devices in creating and handling hanging drops of fluid. The present disclosure also relates generally to cell culture devices, systems and methods of using such devices. The present disclosure also relates generally to the use of cell culture devices for research and high throughput screening.

BACKGROUND OF THE INVENTION

In vitro cellular and tissue models for various drug testing and screening experiments are often central to the development of novel therapeutics in the pharmaceutical industry. Currently, however, most in vitro studies are still performed under conventional two-dimensional (2D) cell culture systems, which are often not physiological models for functional tissues and tumors. Therefore, drug studies involving such models may not produce accurate readouts. To obtain more meaningful results, in vivo studies involving animals are often utilized. However, one obvious drawback of in vivo studies is the time-consuming and expensive nature of these experiments. To bridge this gap between the non-physiological conventional 2D models and in vivo experiments, three-dimensional (3D) in vitro models that provide more therapeutically predictive and physiologically relevant results for drug testing and screening in the pharmaceutical industry are needed. One way to create 3D cell culture models is through the formation of spheroids, or 3D clusters or aggregates of cells.

Scaling up of spheroid culture in a manner suitable for certain applications such as high-throughput screening and testing has several drawbacks. Traditional spheroid formation involves cultivation of suspended cells in hanging drops on the underside of a Petri dish lid. This process requires inverting of the lid following placement of the drops. As a result, the drops are susceptible to perturbation, resulting in falling, spreading, and merging with neighboring drops. Although inexpensive, this method is labor-intensive, does not permit efficient scalable production, and is not compatible with automated instruments for high-throughput screening. Because it is difficult to perform media exchange without damaging the spheroids, this method usually requires another labor-intensive step of transferring the spheroids manually, one by one, to a multi-well culture plate for longer-term culture, treatment, analysis, and harvest.

An alternative is to induce the formation of spheroids under continuous agitation of cell suspension in bioreactors, such as spinner flasks and rotary culture vessels. This method requires the consumption of large quantities of culture media. It also requires specialized equipment and the size and uniformity of the spheroids are hard to control. The high variability in spheroids prohibits their use in many applications.

Methods are also available to produce spheroids using 3D microwell structures and planar micropatterns. However, these methods require specialized and expensive equipment for generating the microwell structures and micropatterns. Moreover, since a plurality of spheroids is cultured within one fluid compartment, the spheroids cannot be individually monitored, manipulated, and treated with testing compounds. The difficulty of performing analysis on individual spheroids before and after treatment also makes these methods unsuitable for certain applications, for example, drug testing and screening applications.

Other recent advances include microfluidic devices designed to generate and manipulate spheroids. However, these devices are expensive to design and produce. In addition, these devices are not suitable for long-term culture of spheroids, not chemically compatible with certain drugs, and not compatible with automated instruments for performing high-throughput screening.

To address problems in the art, there is a need for the devices, methods and/or systems disclosed herein.

SUMMARY

The present disclosure relates generally to devices, systems, and methods of using such devices in creating and handling hanging drops of fluid. The present disclosure also relates generally to cell culture devices, systems and methods of using such devices. The present disclosure also relates generally to the use of cell culture devices for research and high throughput screening.

For example, in some embodiments, the disclosure provides a system, comprising: a) at least one array plate, the at least one array plate comprising a top surface and a bottom surface and a plurality of holes therein, wherein each of the plurality of holes comprises a top and a bottom and wherein the bottom surface of said array plate comprises a at least one plateau substantially adjacent to the bottom of at least one of the plurality of holes; and b) wherein the at least one array plate is configured to accommodate a plurality of hanging drops, wherein each drop hangs from a corresponding one of the plurality of said holes and extends beneath the hole, wherein the number of hanging drops the that at least one array plate can accommodate is equal to or less than the number of holes in the at least one array plate. In certain embodiments, the system further comprises at least one second plate positioned below said at least one array plate. In certain embodiments, the at least one array plate further comprises at least one reservoir. In certain embodiments, one or more of the plurality of hanging drops contains one or more of the following: a plurality of cells; at least one complex tissue or organisms; an aqueous fluid containing biological and/or chemical entities; one or more proteins; one or more nanoparticles, one or more test compounds; one or more drugs; solid or gel formed by aqueous liquid; or combinations thereof. In certain embodiments, the at least one array plate, the at least one second plate, and/or the at least one lid is treated in order to modify to properties of the corresponding treated surface. In certain embodiments, the system may comply with American National Standards Institute and/or Society for Biomolecular Sciences standards. In certain embodiments the system is compatible with high-throughput screening. In certain embodiments, the at least one plateau on the bottom surface of the at least one array plate is configured to stabilize a geometry of said plurality of hanging drops. In certain embodiments, the at least on plateau on the bottom surface of the at least one array plate is configured to stabilize a position of said plurality of hanging drops. In certain embodiments, the at least one array plate is configured to stabilize and maintain measurable properties of said plurality of hanging drops. In certain embodiments, the at least one array plate further comprises at least one plateau on the top surface substantially adjacent to the top of at least one of the plurality of holes, wherein said at least one plateau on the top surface of said at least one array plate is configured to improve a transfer of liquids in and/or out of the holes. In certain embodiments, the system is configured to maintain a substantially stable humidity. In certain embodiments, the system is configured to maintain measurable properties of the environment of the plurality of hanging drops. In certain embodiments, the system is configured to handle small volumes of fluid. In certain embodiments, the system is configured to permit long term culturing of a plurality of cells within the one or more plurality of hanging drops. In certain embodiments, the system is configured to permit one or more of the following: long terms culturing, maintaining, analysis and/or testing of a plurality of cells; long term culturing, maintaining, analysis and/or testing of at least one complex tissue or organisms; long term culturing, maintaining, analysis and/or testing of an aqueous fluid containing biological and/or chemical entities; long term culturing, maintaining, analysis and/or testing of one or more proteins; long term culturing, maintaining, testing and or analysis of one or more nanoparticles; long term culturing, maintaining, analysis and/or testing of one or more test compounds; long term culturing, maintaining, analysis and or testing of one or more drugs; or combinations thereof.

For example, certain embodiments are directed to method(s), comprising: inserting a plurality of hanging drops into a system, comprising: a) at least one array plate, the at least one array plate comprising a top surface and a bottom surface and a plurality of holes therein, wherein each of the plurality of holes comprises a top and a bottom and wherein the bottom surface of said array plate comprises a at least one plateau substantially adjacent to the bottom of at least one of the plurality of holes; and b) wherein the at least one array plate is configured to accommodate a plurality of hanging drops, wherein each drop hangs from a corresponding one of the plurality of said holes and extends beneath the hole, wherein the number of hanging drops that the at least one array plate can accommodate is equal to or less than the number of holes in the at least one array plate; and performing on one or more of the hanging drops culturing, maintaining, analysis, testing, or combinations thereof.

For example, certain embodiments are directed to device(s), comprising: an array plate, comprising a top surface and a bottom surface, wherein the array plate comprises a plurality of holes therein, wherein each hole comprises a top surface and a bottom surface and wherein the bottom surface of said array plate comprises at least one plateau either adjacent, or substantially adjacent, to the bottom surface of one or more of said holes.

For example, certain embodiments provide a device, comprising: a) one or more array plates comprising a top surface and a bottom surface, wherein each of the array plates comprises a plurality of rows and columns of holes therein, wherein each hole comprises a top surface and a bottom surface and wherein the bottom surface of the array plate comprises a plateau adjacent to the bottom surface of each of the holes; and b) a reservoir plate (e.g., a 96 well plate) located below the array plate, wherein the reservoir plate contacts the edges of the array plate (e.g., only the edges), and wherein the reservoir plate does not contact the holes. In some embodiments, the device further comprises a cover for the device, wherein the cover is placed on top of the array plate and wherein the cover does not contact the holes. In some embodiments, the reservoir comprises an aqueous liquid. In some embodiments, the device is fabricated from a polymeric plastic (e.g., polystyrene). In some embodiments, the array plate comprises 384 holes. In some embodiments, the holes are approximately 1.6 mm in diameter. In some embodiments, the holes are approximately 4.5 mm apart. In some embodiments, the device further comprises additional plateaus, or ring structures, adjacent, or substantially adjacent, to the top and/or bottom of at least one side (e.g., both sides) of the holes. In some embodiments, the edge of the plateau comprises a ring structure (e.g., to stabilize droplets). In some embodiments, surface treatment (e.g. coatings, plasma treatment, etc.) is performed on one or more elements of the devices.

Certain embodiments provide a system, comprising: a) one or more array plates comprising a top surface and a bottom surface, wherein each of the array plates comprises a plurality of rows and columns of holes therein, wherein each hole comprises a top surface and a bottom surface and wherein the bottom surface of the array plate comprises a plateau substantially adjacent to the bottom surface of each of the holes; b) a reservoir plate located below the array plate, wherein the reservoir plate contacts the edges of the array plate (e.g., only the edges), and wherein the reservoir plate does not contact the holes; and c) a plurality of hanging drops of fluid, wherein the drops hang from one or more of the holes and extend beneath the hole. In some embodiments, the hanging drops contain a plurality of cells. In some embodiments, the cells remain in suspension. In other embodiments, the cells form aggregates or clusters or spheroids. In some embodiments, the cells are complex tissues or organisms, for example, embryos, tissues, small organisms, worms, etc. In other embodiments, the hanging drops are aqueous fluids containing biological and/or chemical entities or combinations thereof. Examples of the said entities include proteins, nanoparticles, and hydrogels. In some embodiments, the cells are cancer cells (e.g., growing in a spheroid). In some embodiments, the system further comprises a test compound (e.g., an anti-cancer drug). In some embodiments, the system further comprises a lid, wherein the lid covers the array plate but does not contact the cells. In some embodiments, the array plate, reservoir and cover are wrapped with a film that prevents, or inhibits, moisture loss. In some embodiments, the system further comprises one or more high throughput sample handling devices (e.g., robotic sample handling devices or plate readers).

The present disclosure additionally provides methods, comprising: a) inserting a plurality of hanging drops of fluid into a device comprising i) one or more array plates comprising a top surface and a bottom surface, wherein each of the array plates comprises a plurality of rows and columns of holes therein, wherein each hole comprises a top surface and a bottom surface and wherein the bottom surface of the array plate comprises a plateau substantially adjacent to the bottom surface of each of the holes; and ii) a reservoir plate located below the array plate, wherein the reservoir plate contacts the edges of the array plate (e.g., only the edges), and wherein the reservoir plate does not contact the holes, wherein the drops hang one or more of the holes and extend beneath the hole of the array plate; and b) culturing cells in the hanging drops under conditions such that the cells grow and/or maintain viability In some embodiments, the cells are cancer cells, embryonic stem cells, hepatocytes, etc. (e.g., growing in a spheroid). In some embodiments, the method further comprises the step of contacting the cells with a test compound (e.g., a drug, chemical, vapor, biomolecule or nanoparticle) and assaying the effect of the test compound on the growth or other properties of the cells. In some embodiments, hanging drops are placed from the top or bottom of the array plate through the hole or at one opening of the hole. In some embodiments, the method further comprises the step of adding additional liquid and/or cells to the hanging drops by dispensing the liquid into the hole or at one opening of the hole. In some embodiments, the method further comprises the step of removing the liquid and/or cells through the holes. In some embodiments, different portions of the array plate (e.g., different hanging drops or populations of cells) are exposed to different test compounds and/or growth conditions.

Certain embodiments are direct to a system, comprising an array plate, a lid, and a tray, wherein the array plate comprises a top surface and a bottom surface, a reservoir and a plurality of holes or access holes therein, wherein each access hole comprises a top surface and a bottom surface, wherein the bottom surface of the array plate comprises one or more plateau structures either adjacent, or substantially adjacent, to the bottom surface of the plurality of access holes, and wherein the top surface of the array plate comprises a second plateau structure or structures either adjacent, or substantially adjacent, to the top surface of the plurality of access holes. In certain system embodiments, the lid and the tray enclose, or substantially enclose the array plate to isolate the cell culture from external environment and substances. In certain embodiments, the array plate, the lid, and the tray are made of the same material. In other embodiments, one or more of the array plate, the lid and the tray are made of different materials. In some embodiments, the system is substantially airtight. In other embodiments, the system is sufficiently air tight to allow gas exchange between inside and outside of the system and/or maintain humidity inside the system. In some embodiments, either or both the array plate and the tray contain a reservoir that comprises of an aqueous liquid. In some embodiments, the aqueous liquid provides vapor to maintain the humidity inside the system. In other embodiments, the reservoir comprises other substances. In some embodiments, the bottom surface of the tray is substantially optically transparent. In some embodiments, the substantially optically transparent surface is substantially flat and provides a substantially unobstructed view of the cell culture for optical imaging and analysis, such as microscopic, colorimetric, fluorescence, and luminescence imaging and measurements. In some embodiments, the system (or systems) has geometries and measurements that comply with standards, for example present standards set by ANSI/SBS (American National Standards Institute/Society for Biomolecular Sciences), thus making the system compatible with mainstream imaging systems and automated equipment used in research and development (e.g. high-throughput screening).

Additional embodiments are described herein.

DESCRIPTION OF THE FIGURES

The accompanying figures facilitate an understanding of the various, non-limiting embodiments of this technology.

FIG. 2 shows (a) Osmolality of COS7, mES, and A431.H9 cell spheroids with various cell populations over 7 to 12 days of culture, according to certain embodiments. (b) Fluorescence images of live/dead stained COS7 and mES cell spheroids over a 12-day culture. (c) A431.H9 Spheroid Size (Diameter) vs. Initial Cell Number. (d) A431.H9 Spheroid Size (Volume) vs. Time for various initial number of cells/spheroid, according to certain embodiments.

FIG. 4 shows 5-FU results, time-lapse images of A431.H9 spheroids at various concentrations, bar graph outlining percent of control cell viability at various concentrations for all spheroid sizes and conventional 2D culture condition 96 h after drug treatment, according to certain embodiments.

FIG. 15 shows Z-factors for fluorescence-based and absorbance-based assays calculated at various different concentrations, according to certain embodiments.

FIGS. 16A-F illustrates an exemplary array plate, according to certain embodiments. FIG. 16A shows a top view; FIG. 16B shows an isomeric view from top; FIG. 16C shows a side view; FIG. 16D shows an end view; FIG. 16E shows a cross section view along the section line M-M shown in FIG. 16A; and FIG. 16F shows a cross section view of the array plate along the section line L-L shown in FIG. 16C.

FIGS. 17A-D illustrates exemplary plateau structures, according to certain embodiments. FIG. 17A shows a top view; FIG. 17B shows an isomeric view from top; FIG. 17C shows a bottom view; FIG. 17D shows an isomeric view from bottom.

FIG. 20E shows a cross section view along the section line P-P shown in FIG. 20A; and FIG. 20F shows a cross section view of the tray along the section line N-N shown in FIG. 20C.

FIGS. 21A-F illustrate an exemplary lid that the array plate shown in FIG. 16 may be used with, according to certain embodiments. FIG. 21A shows a top view; FIG. 21B shows an isomeric view from top; FIG. 21C shows a side view; FIG. 21D shows an end view; FIG. 21E shows a cross section view along the section line R-R shown in FIG. 21A; and FIG. 21F shows a cross section view of the lid along the section line T-T shown in FIG. 21C.

FIGS. 22A-F illustrates an exemplary assembly of combined array plate, tray and lid, according to certain embodiments. FIG. 22A shows a top view; FIG. 22B shows an isomeric view; FIG. 22C shows a side view; FIG. 22D shows an end view; FIG. 22E shows a cross section view along the section line V-V shown in FIG. 22A; and FIG. 22F shows a cross section view of the assembly along the section line U-U shown in FIG. 22C.

FIGS. 23 A and B illustrate an exemplary stacking of the assemblies shown in FIGS. 22A-F, according to certain embodiments. FIG. 23A shows a side view and FIG. 23B shows an end view.

FIGS. 24A-D illustrate exemplary variations of access hole structure, according to certain embodiments. FIG. 24A shows an exemplary access hole structure with a tall and thin plateau structure on the top surface. FIG. 24B shows an exemplary access hole structure with a short and thin plateau structure on the top. FIG. 24C shows an exemplary access hole structure with a tall and thick plateau structure on the top. FIG. 24D shows an exemplary access hole structure with a tall and thin plateau structure on the top, with a different split line for injection molding.

DEFINITIONS

Figure 1:
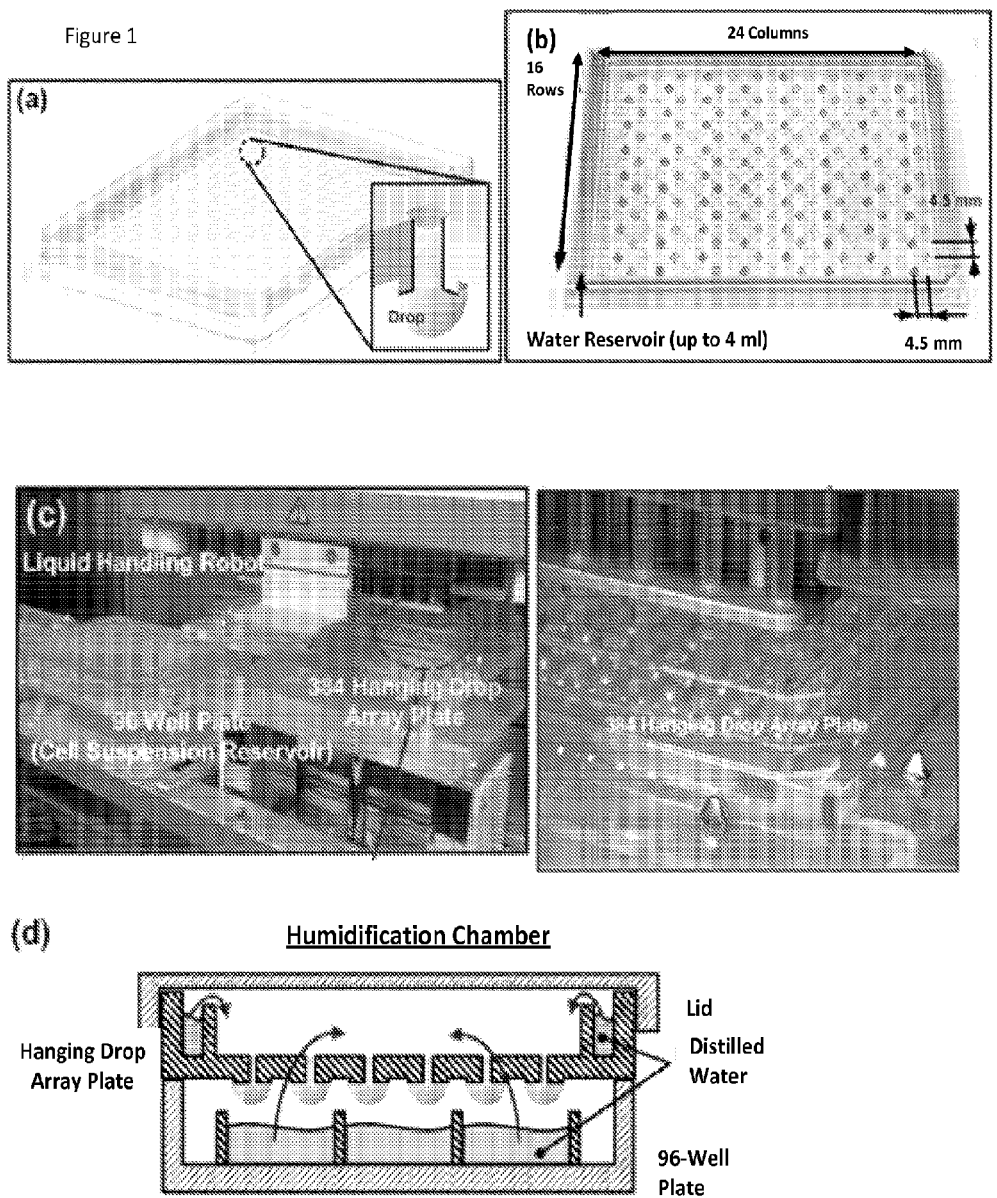
FIG. 1 shows exemplary devices according to certain embodiments of the present disclosure. (a) Illustration of a 384-well formatted cell spheroid culture array plate used in embodiments of the present invention, and its cross-sectional view. (b) Photo and dimensions of the array plate. (c) Photo of the array plate operated with liquid handling robot capable of simultaneously pipetting 96 cell culture sites. (d) Diagram of humidification chamber.

To facilitate an understanding of the present disclosure, a number of terms and phrases are defined below, or terms may be defined elsewhere in the disclosure:

The term "sample" is used in its broadest sense. On the one hand it is meant to include a specimen or culture. On the other hand, it is meant to include both biological and environmental samples.

Biological samples may be animal, including human, fluid, solid (e.g., stool) or tissue, as well as liquid and solid food and feed products and ingredients such as dairy items, vegetables, meat and meat by-products, and waste. Biological samples may be obtained from the various families of domestic animals, as well as feral or wild animals, including, but not limited to, such animals as ungulates, bear, fish, lagamorphs, rodents, etc or combinations thereof.

Environmental samples include environmental material such as surface matter, soil, water and industrial samples, as well as samples obtained from food and dairy processing instruments, apparatus, equipment, utensils, disposable and non-disposable items or combinations thereof. These examples are not to be construed as limiting the sample types applicable to the present disclosure.

As used herein, the term "cell" refers to any eukaryotic or prokaryotic cells (e.g., bacterial cells such as E. coli, yeast cells, mammalian cells, avian cells, amphibian cells, plant cells, fish cells, and insect cells), whether located in vitro or in vivo or combinations thereof. The term "cell" also refers to aqueous fluids or solutions containing one or more cells in a suspension or in clusters or aggregates.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), other cell population maintained in vitro, or combinations thereof.

The term "transfection" as used herein refers to the introduction of foreign nucleic acid into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers may not be dominant in that their use must be in conjunction with a cell line that lacks the relevant enzyme activity. Examples of non-dominant selectable markers include the thymidine kinase (tk) gene that is used in conjunction with tk-cell lines, the CAD gene that is used in conjunction with CAD-deficient cells and the mammalian hypoxanthine-guanine phosphoribosyl transferase (hprt) gene that is used in conjunction with hprt-cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used, the term "eukaryote" refers to organisms distinguishable from "prokaryotes." It is intended that the term encompass organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and/or cell culture. The term "in vivo" refers to the natural environment (e.g., an animal or a cell) and to processes or reactions that occur within a natural environment.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound may be determined to be therapeutic by screening using the screening methods, devices, and/or systems of the present disclosure. In certain embodiments of the present disclosure, test compounds may include antisense, siRNA and/or shRNA compounds.

The term "spheroid" refers to clusters or aggregates of cells and/or cell colonies. Spheroids may be formed from various cell types, for example, primary cells, cell lines, tumor cells, stem cells, etc. Spheroids may have sphere-like or irregular shapes. Spheroids may contain heterogeneous populations of cells, cell types, cells of different states, such as proliferating cells, quiescent cells, and necrotic cells.

DETAILED DESCRIPTION

The following description is provided in relation to several embodiments which may share common characteristics and features. It is to be understood that one or more features of one embodiment may be combinable with one or more features of the other embodiments. In addition, a single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The subject headings used in the detailed description are included only for the ease of reference of the reader and should not be used to limit the subject matter found throughout the disclosure or the claims. The subject headings should not be used in construing the scope of the claims or the claim limitations.

In some embodiments, the devices may combine both 2D and 3D cell culture. For example, in some embodiments, some cells may be cultured on the inner wall of access holes (2D cell culture) while other cells are cultured as spheroids in hanging drops on the bottom surface of the access holes (3D cell culture). For example, in some embodiments, the devices may comprise access holes and well structures found on conventional multi-well plates, allowing both 3D and 2D culture of cells to be performed on the same devices. In other embodiments, the fluids in the access holes and wells may be connected, allowing interactions between cells in the access holes and the wells through secretion and/or detection of cellular products (e.g., chemical and biological molecules).

Spheroids may serve as excellent 3D models for tumors and/or other functional tissues. Spheroids are spherical clusters of cell colonies that may be formed by self-assembly when cell-cell interactions dominate over cell-substrate interactions. Spheroids may be generally be defined as clusters or aggregates of cells and/or cell colonies that may be formed by self-assembly when cell-cell interactions dominate over cell-substrate interactions. Spheroid may be formed from various cell types, for example, primary cells, cell lines, tumor cells, stem cells, etc. Spheroids may have spherical or irregular shapes. Spheroids may contain heterogeneous populations of cells, cell types, cells of different states, such as proliferating cells, quiescent cells, and necrotic cells. Spheroids may mimic tumors and may serve as excellent physiologic tumor models known to provide more reliable and meaningful therapeutic readouts. Spheroids may produce results and/or measurements that are consistent and/or reproducible. For example, samples subjected to the same treatment in the same experiment or replicates of the same experiment produce measurements that are consistent or within acceptable ranges of standard deviation, for example, within 10 to 30%. Other acceptable ranges are also contemplated. This means that the results and/or measurements obtained are of relevance and value to the subject being investigated. For example, samples may produce results and/or measurements that closely mimic outcomes produced from in vivo, animal, and/or human studies. This may include quantitative and/or qualitative results that follow similar trend or within acceptable numerical ranges, for example 10 to 30%, from measurements obtained from in vivo, animal, and/or human studies. Other acceptable ranges are also contemplated. Although these advantages of spheroids have been recognized, the tedious and challenging procedures required for formation, maintenance, solution exchange, and microscale cell and fluid manipulation are still holding back the industry from using the well-validated spheroid tissue model more widely. Furthermore, due to the complexities of 3D models, it has been difficult to scale up 3D culture in a high-throughput manner for screening and testing purposes.

Typical spheroid formation methods include hanging drops, culture of cells on non-adherent surfaces, spinner flask cultures, and NASA rotary cell culture systems. However, these traditional spheroid formation and culture systems are often very tedious, not high-throughput, and hard to handle. Various microfluidic (spheroids on a chip) devices have also been developed to increase spheroid formation efficiency. Many of these techniques, however, still suffer from problems such as long-term culture and device compatibility with drugs. In addition, many of these microfluidic devices are not compatible with various existing high-throughput screening (HTS) systems, and thus, cannot be commercialized to benefit the pharmaceutical industry.

Experiments conducted during the course of development of certain embodiments of the present disclosure resulted in the development of high-throughput hanging drop array systems that allow for efficient formation of uniformly-sized spheroids and/or long-term spheroid cultures in a standardized plate format compatible with various commercially available HTS systems, which make these systems ideal for commercialization for wider use.

Certain embodiments of the devices, methods and/or systems described herein overcome, for example, obstacles to robust drop handling such as difficulty of guiding fluid to regions of the plate that the fluid is to go to without the fluid spreading to other parts of the plate caused by, for example, inaccuracies in pipette positioning, spreading of the liquid beyond regions of the plate desired due to, for example, vibration, movement, spreading of the liquid by wetting or combinations thereof. For example, certain embodiments result in more robust drop handling due in part to the plateau structures at the bottom of the plate that allow hanging drops of highly reproducible geometry and size to be formed in confined locations without spreading or with minimal spreading. Other embodiments result in easy transfer of reproducible volumes of fluids in and out of access holes. Other embodiments result in easier, faster, and more accurate alignment of liquid handling apparatus, such as pipette tips and transfer pins, with the access holes.

Certain embodiments are directed to handling fluids and/or producing hanging drops of fluid containing one or more of the following: suspension and/or aggregates of cells; complex biological structures, for example, one or more embryos, tissue samples, small organism, worms, etc., or combinations thereof; fluid contains physical, chemical, and/or biological entities; or combinations thereof. Certain embodiments are directed to handling fluids and/or producing hanging drops of fluid wherein said hanging drops contain suspensions and/or aggregates of cells. Certain embodiments are directed to handling fluids and/or producing hanging drops of fluid wherein said hanging drops contain complex biological structures, for example, one or more embryos, tissue samples, small organism, worms, etc. or combinations thereof. Certain embodiments are directed to handling fluids and/or producing hanging drops of fluid wherein said hang drops contains physical, chemical, biological entities, or combinations thereof.

Certain embodiments are directed to handling fluids and/or producing hanging drops of fluid wherein: cell suspensions and/or aggregates may be grown, maintained, tested, analysis or combinations thereof; one or more proteins may be crystallized by evaporation in hanging drops and/or analyzed; nanoparticles may be observed and/or analyzed in the hanging drops; the hanging drops serve as reactors for chemical, physical, and/or biological changes to take place; or combinations thereof. Certain embodiments are directed to handling fluids and/or producing hanging drops of fluid wherein cell suspensions and/or aggregates may be grown, maintained, tested, analysis or combinations thereof. Certain embodiments are directed to handling fluids and/or producing hanging drops of fluid wherein one or more proteins may be crystallized by evaporation in hanging drops, analyzed, or combinations thereof. Certain embodiments are directed to handling fluids and/or producing hanging drops of fluid wherein nanoparticles may be observed and/or analyzed in the hanging drops. Certain embodiments are directed to handling fluids and/or producing hanging drops of fluid wherein the hanging drops serve as reactors for chemical, physical, biological changes to take place, or combinations thereof.

Certain disclosed embodiments improve on ease of liquid transfer. For example, in certain embodiments, the plateau structures on the top surface of the access holes make it easy to align pipette tips or transfer pins with the access holes during liquid transfer whether liquid handling is perform manually or using automated systems. The plateau structures on the top surface may also prevents spilling or spread of liquids from one access hole to another.

Cells normally grow in 3D conditions, so in order to obtain accurate and meaningful therapeutic readouts, new 3D screening and testing platforms, such as 3D spheroid culture, that mimic physiological microenvironments in a high-throughput fashion are useful in the pharmaceutical industry as well as other industries. By accurate and meaningful, it is intended, for example, that results and/or measurements obtained are of relevance and value to the subject matter being investigated. For example, samples may produce results and/or measurements that closely mimic outcomes produced from in vivo, animal, and/or human studies. This may include quantitative and qualitative results that follow similar trend or within acceptable numerical ranges, for example 10 to 30%, from measurements obtained from in vivo, animal, and/or human studies. Other acceptable numerical ranges are also contemplated and depend on the measurements being sought.

Intricate devices that provide efficient and/or high-throughput culture of cells in physiological microenvironments have been developed. However, most of these intelligent devices created in academic laboratories lack the capability to be commercialized for wider use in the industry. Experiments conducted during the course of development of certain embodiments of the present disclosure resulted in the development of various spheroid formation and culture hanging drop array plates compatible with various commercially available HTS instruments and tools for high-throughput spheroid formation and long-term culture. These systems efficiently form spheroids as excellent physiological 3D tissue and tumor models for drug screening and testing as well as other cell-based applications or combinations thereof. In certain embodiments, long-term culture generally means that cells and/or aggregates of cells can be kept in viable state for durations longer than conventional methods of spheroid culture, for example, for over 1 week to 6 weeks or longer. Although as disclosed herein other time frames are contemplated. This is possible because culture media can be readily exchanged through the access holes using manual pipetting and/or automated liquid handling systems to maintain the adequate conditions (such as nutrient level) for spheroid growth and survival. This allows spheroids to be continuously cultured on the array plate, without the need to be transferred to a separate container after the spheroids have exceeds certain size or culture time due to limited available nutrients in the media.

High-throughput screening (HTS), generally means that the embodiment is compatible with microscopy, analytical, and/or automated systems that are used in drug discovery and relevant fields of chemistry and biology. One system (or a combination of these systems) allows researchers to perform large number of tests, for example 100 to 100,000 tests, in a day. In certain embodiments, the number of tests that can be performed may be 100 to 10,000, 500 to 10,000, 100 to 20,000, 1000 to 30,000, 1000 to 50,000, 10,000 to 80,000, etc. HTS allows researchers to identify chemical and biological entities of relevance and understand biological processes. Mainstream HTS instruments are designed to perform operations or tasks, such as liquid handling, imaging, microscopy, or optical detection, on samples contained on a microtiter plate that complies with ANSI/SBS standards. In some embodiments, the device (array plate or combination of array plate with lid and bottom plate) complies with standards, for example present ANSI/SBS standards, therefore allowing the device to be used with HTS instruments, which means the generation and assessment of hanging drops or spheroids can be easily scaled up.

Certain embodiments provide a multiplex (e.g., 1536, 384, 96, etc.) hanging drop array plate that provides easy handling and media exchange procedures. In other embodiments, the access holes are arranged in other suitable multiplex configurations, in row and columns, such as 18 (3 by 6), 25 (5 by 5), 72 (6 by 12), 100 (10 by 10), or 625 (25 by 26) holes. The use of standardized (e.g., 16 by 24 384-well, 8 by 12 96-well) formats that comply with standards, for example present standards set by ANSI/SBS (American National Standards Institute/Society of Biomolecular Sciences), offers compatibility with most commercially available HTS instruments. Hanging drop formation and subsequent culture media exchange procedures using the liquid handling robot are demonstrated in FIG. 1c. The hanging drop array plates described herein find use, for example, as a high-throughput 3D screening/testing platform for a variety of applications.

The devices, methods and/or systems of certain embodiments of the present disclosure provide one or more advantages over the currently available devices. Some advantages include, but are not limited to, the ability to grow cells of uniform and adjustable cellular aggregate size (e.g., size/volume of cellular aggregate may be control by geometry of plate structure, cell seeding number, or culture time); compatibility with existing high-throughput screening instruments, such as, for example, liquid handling systems and plate readers; suitability for the formation of physiologically relevant models (e.g., by mimicking oxygen gradient, diffusion transport, and distribution of cells found in solid tumors and tissues); suitability for high-throughput screening; suitability for mass production of cellular aggregates; suitability for long term culture of cellular aggregates; provide efficient gas exchange due to maximum surface contact of cultured droplets with gas; efficient transfer (pipetting) of content to and from the plate during cell seeding, media exchange, and reagent addition and removal; ease of addition and removal of cells, media, reagents, and other contents during different time points of an experiment; harvest of cellular aggregates from both top and bottom of the plate; reduction in labor, time, and costs or combinations thereof. Cost are reduced, for example, via streamlining and simplification of the growth and testing of cellular aggregates, formation, maintenance since assay of cellular aggregates are conducted on the same plate and easy to carry out, efficient formation of cellular aggregates (e.g., standard 384-well format reduces consumption of test compounds and reagents and multi-well format means time spent dispensing liquid is reduced and the number of plate manipulation for a fixed number of endpoints is also fewer) or combinations thereof.

Other advantages of certain embodiments are the minimal consumption of culture media and/or minimal quantities of drugs or other test compounds required in cell treatment. Because the spheroids are grown in individual droplets of culture medium in small volumes, for example, less than 100 to 20 microliter, substantially less culture media is needed for spheroid culture. Consequently, substantially less drugs and testing compounds are needed in treatment of the cells to achieve the desired drug concentrations in the droplets. In certain embodiments, the volume of the droplets may be less than 200, 125, 100, 80, 60, 40, 20, or 10 microliters. In certain embodiments, the volume of the droplets may range from 10 to 250, 10 to 200, 20 to 200, 20 to 100, or 100 to 250 microliters.

For example, certain embodiments provide the ability to grow cells of uniform and adjustable cellular aggregate size. In some embodiments, uniform size means that the variation in size or volume of spheroids can be maintained within a small range, such as 3 to 5%, throughout the culture period. In some embodiments, adjustable size means that the final size or volume of spheroids can be controlled by number of cells seeded, length of culture period, and/or other parameters. In certain embodiments, uniform size, may mean the variation in size or volume of spheroids can be maintained within ranges, such as 1 to 10%, 2 to 8%, 2 to 5%, 3 to 8%, 4 to 10%, or 5 to 10% to 5% throughout the culture period or throughout a sufficient portion of the culture period. In certain embodiments, adjustable size means that the final size or volume of spheroids can be controlled by the number of cells seeded, length of culture period, and/or other parameters.

Certain embodiments are compatibility with existing high-throughput screening instruments, such as, for example, liquid handling systems and plate readers. Compatibility with microscopy systems, automated equipment such as liquid handling, detection, and/or imaging systems used in high throughput and high content screening are need advantages that the present disclosure addresses. Certain system embodiments are designed in multi-well plate format that complies with standards, for example present ANSI/SBS standards, which are acceptable by mainstream instruments. Using automated instruments, generation and/or assessment of spheroids can be scaled up using the multiple array plates disclosed herein. The access holes allow liquid to be easily transferred in and out of the droplets for maintenance and treatment of spheroids. Using high-throughput instruments, generation and assessment of spheroids can be easily scaled up using multiple array plates.

Certain embodiments are suitability for the formation of physiologically relevant models (e.g., by mimicking oxygen gradient, diffusion transport, and distribution of cells found in solid tumors and tissues). For example, certain test compounds are more effective for cells residing in the hypoxic core of a spheroid that is similar to solid tumors, where oxygen consumption by cells is active and/or diffusive oxygen transport is limited. For example, certain test compounds are less effective at suppressing growth of quiescent cells, which usually reside in the interior of spheroids and are hard to replicate in 2D cell culture. Therefore, testing conducted on the more proliferative cells in 2D culture would yield results that are less physiologically accurate.

Certain embodiments may be suitability for mass production of cellular aggregates. In some embodiments, each device allows the formation of 384 spheroids in hanging drops. By using automated systems and a plurality of devices, one can form, for example, 1,000 to 100,000 hanging drops, each containing cells that will form spheroids, within a reasonable period of time, for example within 5 minutes, 15 minutes, 1 hour, 2 hours, 5 hours, 10 hours, or 24 hours.

Certain embodiments are suitability for long-term culture of cellular aggregates. For example, in certain embodiments cellular aggregates may be cultured for at least 1, 2, 3, 4, 5 or 6 weeks. For example, in certain embodiments cellular aggregates may be cultured for between 1 to 6 weeks, 1 to 2 weeks, 1 to 4 weeks or 2 to 5 weeks.

Certain embodiments are suitability for culture of cellular aggregates for shorter periods of time as well. For example, in certain embodiments cellular aggregates may be cultured for at least 30 minutes, 1 hour, 2 hours, 3 hours, 5 hours, 8 hours, 12 hours 24 hours, 2 days, 3 days, or 6 days. For example, in certain embodiments cellular aggregates may be cultured for up to 30 minutes, 1 hour, 2 hours, 3 hours, 5 hours, 8 hours, 12 hours 24 hours, 2 days, 3 days, 6 days or 7 days. For example, in certain embodiments cellular aggregates may be cultured for between 30 minutes to 7 days, 2 hours to 24 hours, 30 minutes to 48 hours, 1 hour to 5 days, or 1 hour to 7 days.

Certain embodiments provide efficient gas exchange due in part to maximum surface contact of cultured droplets with gas. For example, in comparison to fluids in conventional multi-well plate, where the top surface of the volume of fluid is exposed to air for gas exchange, hanging drops formed in certain embodiments have a significantly higher proportion of surface area exposed to air for exchange (entire drop surface below the access hole and top opening of the access hole). Efficient gas exchange is often useful in studies where concentration of certain gaseous component (e.g. oxygen) is pertinent to cell behavior.

Certain embodiments provide efficient transfer (pipetting) of content to and from the plate during cell seeding, media exchange, and/or reagent addition and removal; ease of addition and removal of cells, media, reagents, and/or other contents during different time points of an experiment; harvest of cellular aggregates from both top and bottom of the plate; reduction in labor, time, and costs; or combinations thereof. The monitoring and/or manipulation of individual spheroids are other advantages of certain disclosed embodiments. Analysis of individual spheroids before and after treatment also are advantages to certain disclosed embodiments. Because each spheroid is isolated and grows in its own droplet, they can be individually treated with compound, individually monitored and analyzed using microscopy techniques and analytical methods, individually harvested for further processing, or combinations thereof. Furthermore, long-term culture and assessment of individual spheroid for durations ranging from 1 week to 6 weeks are possible. Other time period are also contemplated. Since the culture media can be easily exchanged through the access holes using manual pipetting or automated liquid handling systems to maintain adequate nutrient level for spheroid growth and survival.

Therefore, spheroids do not need to be transferred to larger containers after exceeding certain size or time due to limited available nutrient in the media.

Certain embodiments result in cost being reduced, for example, via streamlining and simplification of the growth and testing of cellular aggregates, formation, maintenance since assay of cellular aggregates are conducted on the same plate and easy to carry out, efficient formation of cellular aggregates (e.g., standard 384-well format reduces consumption of test compounds and reagents and multi-well format means time spent dispensing liquid is reduced and the number of plate manipulation for a fixed number of endpoints is also fewer) or combinations thereof. For example, in comparison to standard tests conducted using conventional 96-well plate where each sample (each well) requires 200 microliters of cell culture media, each sample only requires 20 microliters of media in certain embodiments, reducing the quantity of and cost spent on culture media. Likewise, in some embodiments, 10 times less of test compounds are required to achieve the same treatment concentration in each sample, which is significant as many drugs used in preclinical and clinical experiments are expensive to produce and are produce in extremely low quantities. In comparison to hanging drops formed on the underside of Petri dishes using conventional methods, formation of 384 spheroids in certain embodiments that employ automated system only takes a fraction of the time (and labor), ranging from 1 to 15 seconds, versus 5 to 15 minutes required by the conventional methods, In some embodiments, the devices are distinguished by the ability to harvest cells from the top and/or the bottom of the plate, the ability to include a reservoir (e.g., water reservoir) on one or both of the hanging drop plate and bottom plate; a simple plate design that allows easy molding and mold release during manufacturing and the ability to perform on-plate analysis of cellular aggregates and chemical entities (e.g., the contents of the plate do not need to be harvested into a separate plate, container, or device in order to be analyzed; analysis, such as colorimetric, fluorometric, lumniometric, etc., can be conducted by placing the plate with its contents in a standard high-throughput screening instrument such as a plate reader and direct illumination and detection of optical signals of the cultured droplets can be performed since there is no plastic material underneath the samples as in conventional multiwall plate) or combinations thereof. In other embodiments, the bottom plate is substantially optically transparent and offers unobstructed view of the droplets, allowing illumination and detection of optical signals of the droplets to be performed with the array plate sitting on top of the bottom plate.

In certain embodiments, the bottom plate provides an unobstructed view of the spheroids which make imaging and analysis easier. In certain embodiments, the bottom plate provides unobstructed view of the spheroids on the array plate for convenient imaging of the spheroids, as well as optical analysis of the spheroids.

In order to culture spheroids over various periods of time including a long period of time, the osmolality of the cell culture media in the hanging drops is preferably kept in certain embodiments within a relatively stable range. In certain embodiments, a relatively stable range may be maintaining the desired parameters of the hanging drops to ±1%, ±3%, ±5%, ±8%, ±10%, ±15%, ±20%, or ±25% of the desired or stated parameters. In certain embodiments, a relatively stable range may be maintaining the desired or stated parameters of the hanging drops to a sufficient range of variation such that the end results of the culturing may be achieved or substantially achieved. In certain embodiments, the osmolality of the cell culture media in the hanging drops is kept within a relatively stable range. For example, within 10% to 20% of the initial osmolality measurements. In other examples, within 3% to 20%, 5% to 15%, 5% to 25%, 5% to 10%, or 15% to 20% of the initial osmolality measurements. In certain embodiments, culture of spheroids can be kept in a stable range for 1 to 6 weeks. For example, in certain embodiments culture of spheroids can be kept in a stable range for at least 30 minutes, 1 hour, 2 hours, 3 hours, 5 hours, 8 hours, 12 hours 24 hours, 2 days, 3 days, or 6 days. For example, in certain embodiments culture of spheroids can be kept in a stable range for between 30 minutes to 7 days, 2 hours to 24 hours, 30 minutes to 48 hours, 1 hour to 5 days, or 1 hour to 7 days. Other ranges are also contemplated.

Certain embodiments provide the ability to generate highly reproducibility of spheroid formation in the hanging drops. Because spheroids can be formed with substantially the same initial number of cells, and the spheroids are formed in isolated volumes, the growth of spheroids are highly reproducible and fusing of neighboring spheroids, which produces variation in size, is avoided since contact between individual spheroids is avoided. In certain embodiments, the variation in size between spheroids can be maintained within 3% to 5% throughout the culture period. In certain embodiments, the variation in size between spheroids can be maintained within 3% to 5%, 2% to 6%, 1% to 6%, or 3% to 6% throughout the culture period. In certain embodiments, the variation in size between spheroids can be maintained within 3% to 5%, 2% to 6%, 1% to 6%, or 3% to 6% throughout a substantial portion of the culture period.

In certain embodiment, the stability of droplets may be improved due in part to the plateau structures at the bottom surface of the access holes. The droplets are stabilized and maintained in defined size and location, substantially limiting the spreading of the droplets.

Due to the small volume nature of the hanging drops, evaporation can cause the osmolality of culture media to shift. In some embodiments, in order to prevent this, or substantially prevent this, during spheroid culture, the hanging drop array plate is sandwiched by a well-plate lid and a plate (e.g., 96 well plate) filled with distilled water or other aqueous solutions, and the whole setup is subsequently wrapped in parafilm or other sealing material. The water-filled plate (or aqueous-filled plate) directly on the bottom of the hanging drops provides humidification to the hanging drops. In some embodiments, a water reservoir, or aqueous reservoir, (e.g., as shown in FIGS. 1$b$ and $d$) in the periphery of the plate together with parafilm prevents extensive evaporation from the hanging drops, especially the droplets closer to the sides of the plate where they are more prone to evaporation. With such setup and culture media exchange every other day, the osmolality of mES cell, Cos-7 cell, and A431.H9 cell culture media could be kept in a stable range of 300 to 360 mmol/kg (FIG. 2$a$), which is within the optimal range for cell culture. In certain embodiments, the osmolality of the cell culture media in hanging drops is kept within a relative stable range, for example, within 10 to 20% of the initial osmolality measurements. Live/dead staining images further show that most cells were still alive after 2 weeks of culture. In addition, A431.H9 spheroids at various different sizes all seemed to be proliferating properly over the 1 week period (FIG. 2$c$). Together with the robustness of the hanging drop integrity, the hanging drop array plate system offers long-term culture of spheroids, which would not be possible with the conventional hanging drop systems or methods.

To demonstrate drug screening using an exemplary embodiment, 2 drugs were tested—a non-conventional, hypoxia-sensitive drug tirapazamine (TPZ) and a conventional anti-cancer drug 5-fluorouracil (5-FU), on A431.H9 cells under both 2D and 3D culture conditions. TPZ is a hypoxic cytotoxin that is activated only under hypoxic conditions, resulting in metabolites causing DNA damage. Intracellular reductases convert TPZ to a cytotoxic radical that produces DNA single and double-strand breaks, base damages, as well as chromosome aberrations under low oxygen conditions. Under normal conditions, oxygen causes back-oxidation of the TPZ radical to the non-toxic parent compound, and therefore greatly reduces the cytotoxicity. The effect of TPZ on A431.H9 cells cultured as attached cells under conventional 2D conditions as well as 3D spheroids using a 384 hanging drop array plate was tested. It was found that the $IC_{50}$ of 2D condition (~50 μM) is greater than the $IC_{50}$ of 3D condition (~8 μM). Therefore, contrary to most drug tests, A431.H9 cells are more resistant to TPZ when cultured under conventional 2D condition than 3D spheroid. This is mainly due to the inherent oxygen gradient that exists within 3D spheroids. Because of diffusion limit, spheroids with a diameter greater than 500 μm typically have a hypoxic core in the center and a corresponding oxygen gradient to the outer surface of the spheroid. Since TPZ is a hypoxic drug that is much more cytotoxic under low oxygen conditions, it is more sensitive to the A431.H9 cells cultured as 3D spheroids than in 2D where there is no oxygen gradient. This distinct difference between the $IC_{50}$ obtained from the same drug tested under 2 different culture conditions demonstrates the utility of using 3D models for drug screening and testing purposes. Just like spheroids, inherent oxygen gradients also exist inside solid tumors. 3D tumor models therefore provide much more accurate and meaningful therapeutic readouts. 3D tumor models are useful in screening for drugs that target the quiescent cells in the hypoxic inner parts of tumors.

5-FU is a conventional anti-cancer drug that inhibits cellular proliferation. In the case of 5-FU, it was found that the $IC_{50}$ is greater under 3D (~1 to 100 μM) than 2D condition (~0.1 μM). As expected, A431.H9 cells are more resistant to 5-FU when cultured as 3D spheroids than in 2D condition. Due to the 3D integrity of spheroids, it would be harder for 5-FU to diffuse and penetrate into the center cell mass. Furthermore, 5-FU specifically targets proliferating cells, and thus might not be able kill the quiescent cells in the inner regions of the spheroids. Nevertheless, this demonstrates the importance of 3D models in drug testing and screening applications. 5-FU $IC_{50}$'s found from 2D and 3D testing platforms were very different for A431.H9 cells.

Physiological 3D models provide much more accurate and meaningful results that save time and resources in the long run. Experiments conducted during the course of development of embodiments of the present disclosure overcame the difficulty of scaling up long-term 3D culture of cells in a high-throughput manner by developing a hanging drop array plate in the standardized format compatible with various commercially available high throughput screening instruments.

I. Devices and Systems

The below description provides a detailed description of exemplary devices of embodiments of the present disclosure. The devices described below are exemplary, non-limiting embodiments of the present disclosure. The disclosure is not intended to be limited to the exemplary devices described herein.

Figure 5:
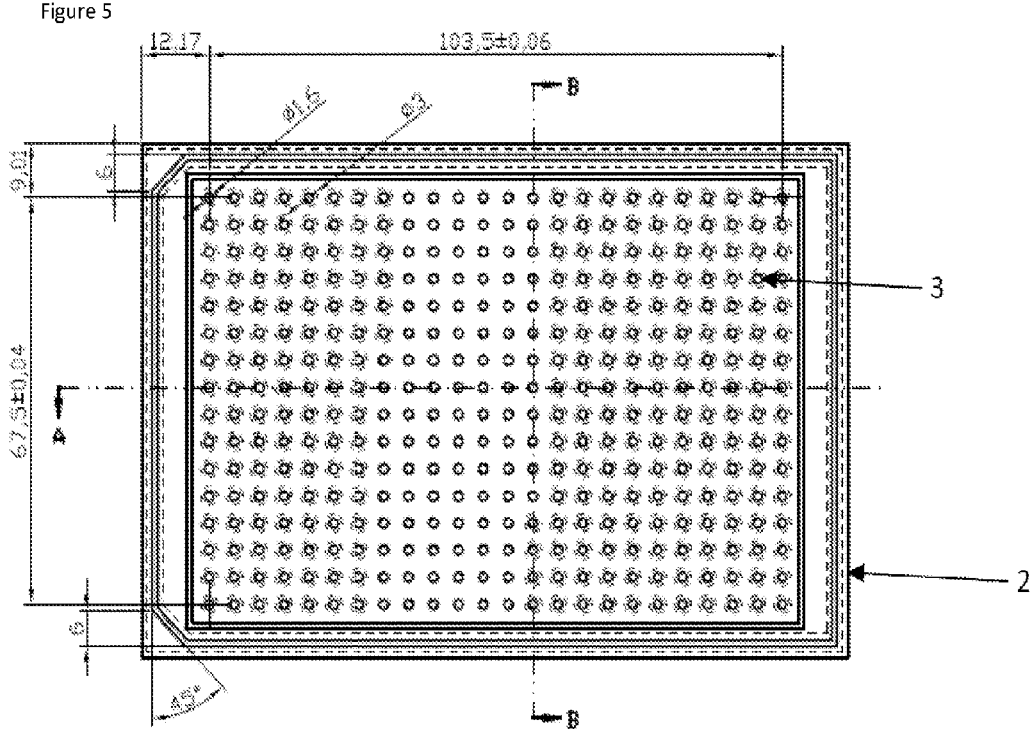
FIG. 5 shows a schematic of an exemplary device used in certain embodiments.
Figure 6:
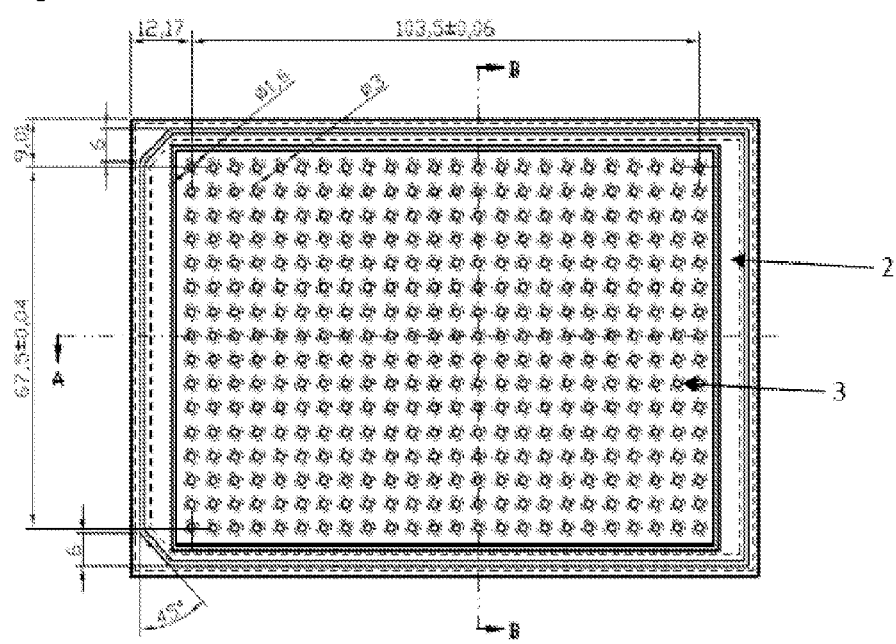
FIG. 6 shows a schematic of an exemplary device used in certain embodiments.

FIG. 5 shows an exemplary assay plate 1. FIG. 6 shows an alternative assay plate 4. Assay plates 1 and 4 each contain a plurality of wells 3. However, it should be understood that the present disclosure is not limited to a particular configuration. Assays plates may contain any number of wells. In some embodiments, a 12×8, 24×16, or other configuration is used. In some embodiments, arrays of multiple array plates (e.g., 24×16 array plates) are used. Assay plates 1 and 4 also comprise a water reservoir 2 along one or more (e.g., all four) edges of the plate.

Figure 7:
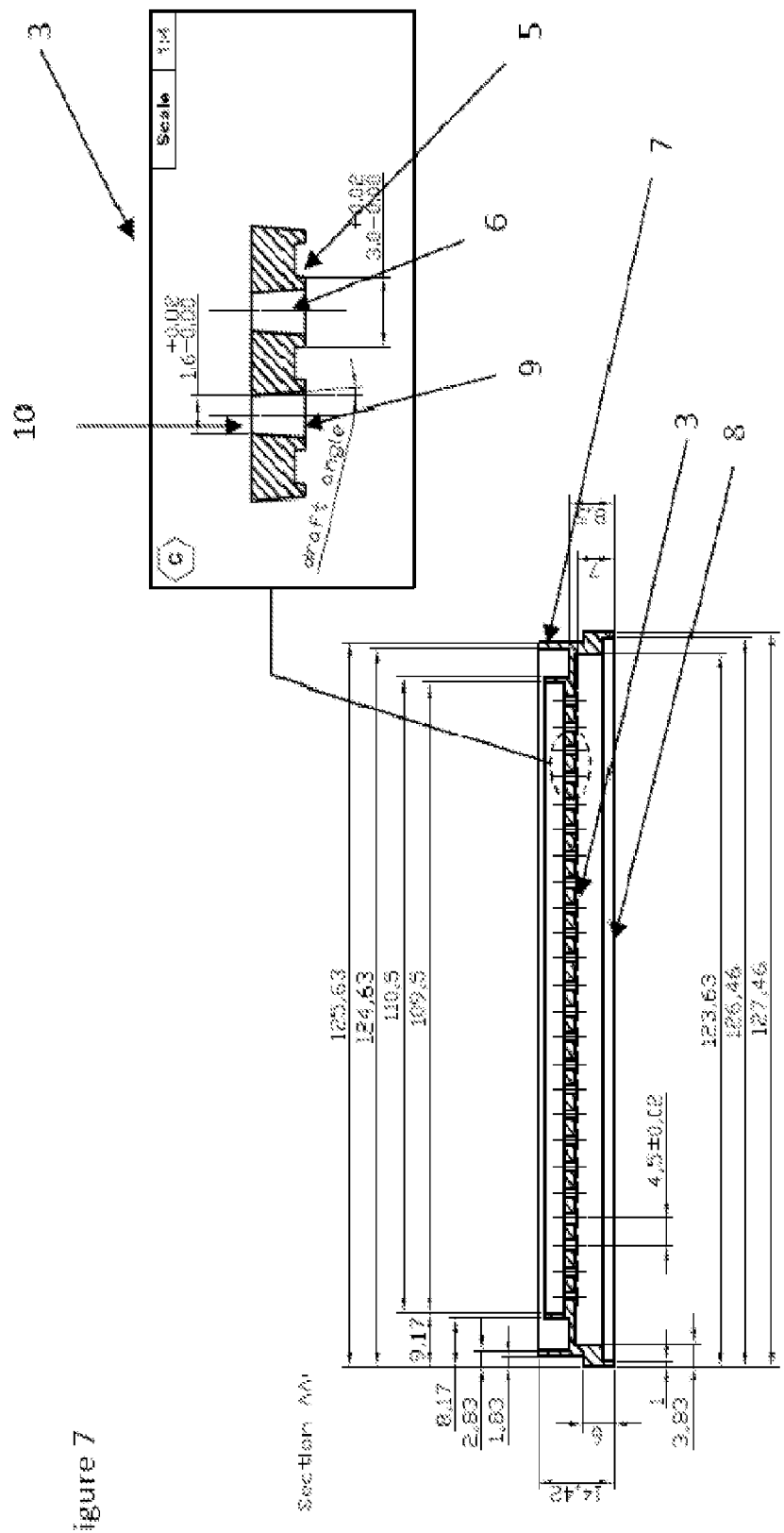
FIG. 7 shows a detailed view of an exemplary device used in certain embodiments.
Figure 8:
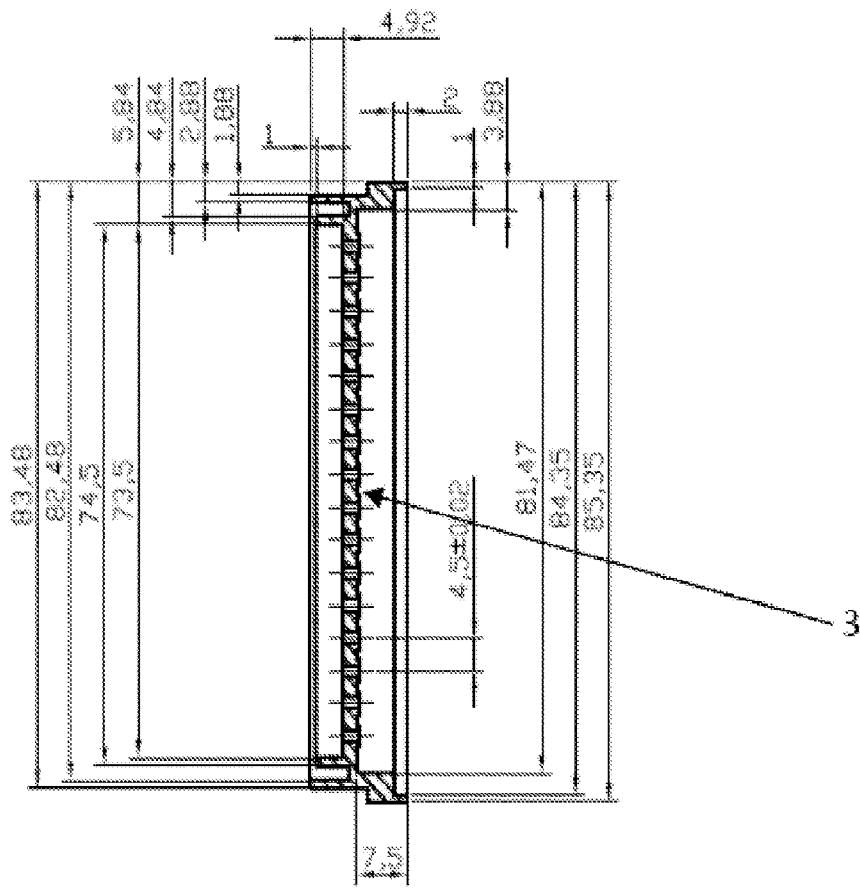
FIG. 8 shows a detailed view of an exemplary device used in certain embodiments.
Figure 9:
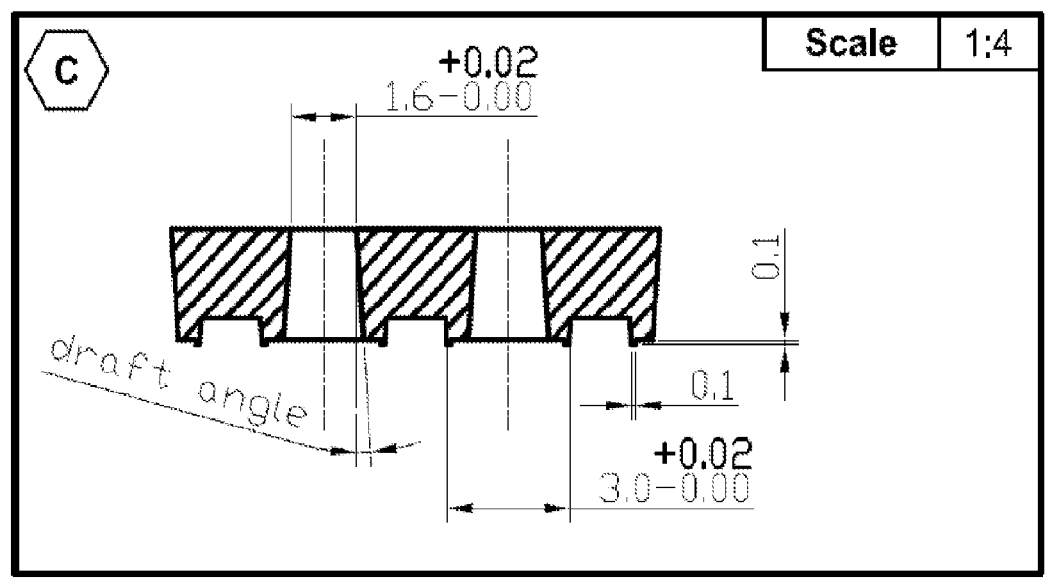
FIG. 9 shows a view of a plateau region, according to certain embodiments.

FIGS. 7 and 8 show cross sections of assay plate 1. The cross sections show wells 3 comprising holes 6 having a bottom surface 9 and a top surface 10. In some embodiments, the holes 6 are approximately 1.6 mm in diameter. In some embodiments, the distance between holes 6 is approximately 4.5 mm. In some embodiments, the wells comprise an additional protrusion, plateau, or ring 5 next to each hole 6. In some embodiments, the protrusions 5 are approximately 0.5 mm in height. FIG. 7 also shows a cross section of the assay plate 1 showing a lid 7 and a microtiter plate (e.g., 96 well plate) 8. The plate 8 is underneath wells 3. In some embodiments, the plate comprises liquid (e.g., water) in the wells of the plate. In some embodiments, the water reservoir in the plate 8 is around the edges or in another location. In some embodiments, one or more water reservoirs are on one or more edges around the plate. In other embodiments, one or more water reservoirs are located at positions that do not interfere, or substantially interfere with the positions of the access holes. In some embodiments, the reservoir contains aqueous fluids. In other embodiments, the reservoir contains hydrogels, such as agarose gel, which is less prone to spill like aqueous fluids and can provide humidifying vapor. In other embodiments, the reservoir contains solids, for example, chemicals that vaporize as testing compounds.

Figure 14A:
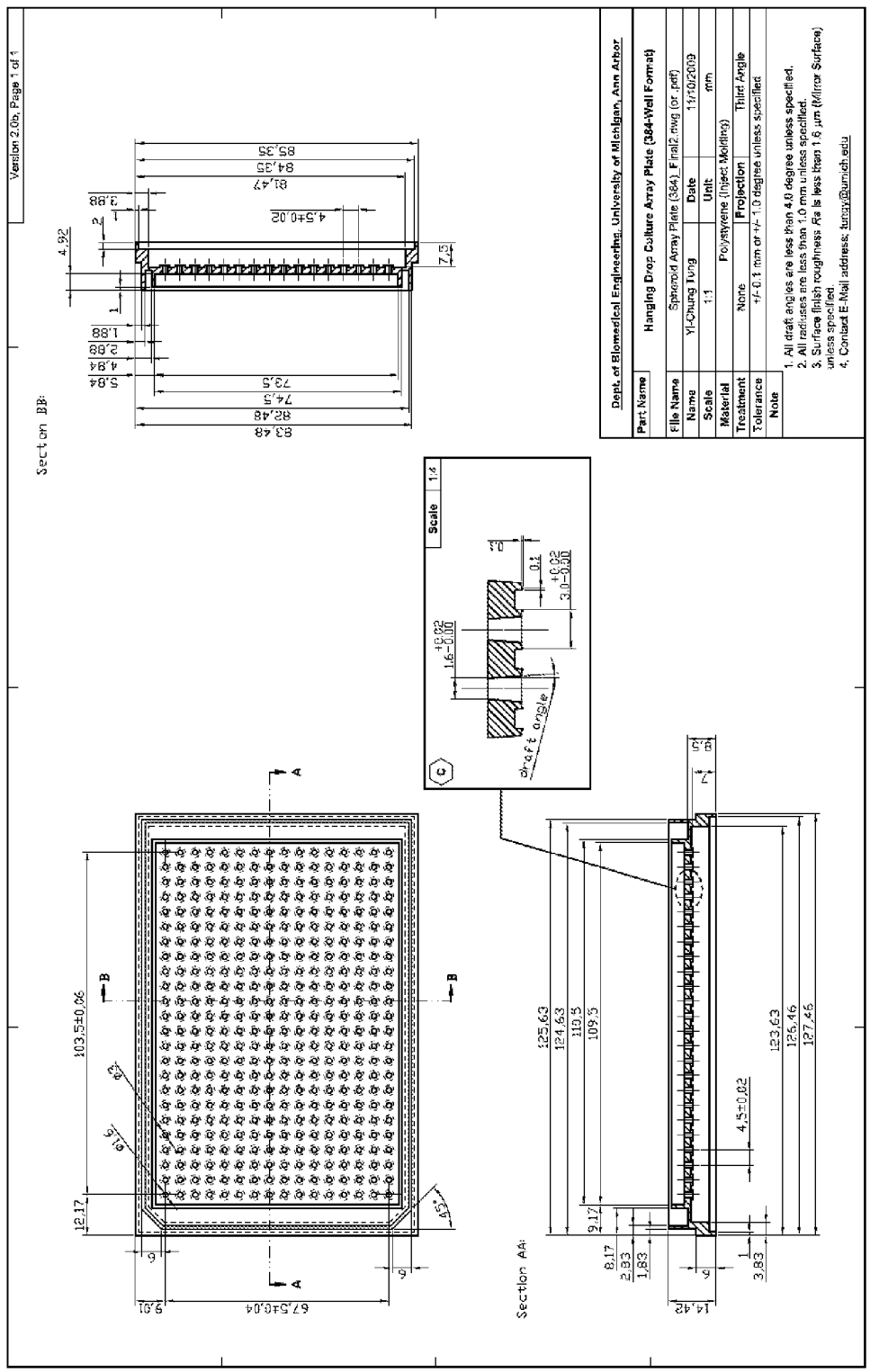
FIG. 14 shows a schematic of an exemplary device used in certain embodiments. A. Overview. B. close up of ring structures.

FIG. 14 shows an additional embodiment of the device. In some embodiments, the device comprises additional rings 11 below and/or above the hole 6. In some embodiments, the rings are 0.25 μM wide, although other sizes are contemplated. In some embodiments, the rings 11 are approximately 0.5 μM in height, as measured from the top of the plate or the bottom of the plateau. In some embodiments, rings 11 located above the hole serve to present liquid from spreading out on the top surface. In some embodiments, rings 11 located on the bottom of the plateau enhance droplet stability.

In some embodiments, the plate 8 contains water, other aqueous fluids, gels, test compounds, sorbent material or combinations thereof.

In some embodiments, drops are inserted into holes 6 via the top surface 10 of hole 6 such that the drops hang from the bottom surface 9 and extend beneath the bottom portion of well 6 into protrusions 5 as shown in FIG. 1A. In some embodiments, the combination of the liquid in the well 8 and the lid 7 provide a humidification chamber for the drops. In some embodiments, the device, including the assay plate, humidification chamber, and cover, is wrapped in a laboratory wrap such as PARFILM wrap to further prevent evaporation.

In some embodiments, devices include a configuration where some contact, contact, or substantial contact between the lid or other component with access holes, hanging drops, and edges is provided (e.g., to transfer cells and reagents to and from plate).

In some embodiments, the plate 8 is a multi-well plate. However, in other embodiments, additional configurations are utilized, including, but not limited to, assay blocks, containers, bed of gel, etc.

FIGS. 16-24 shows additional embodiments. In some embodiments, the device comprises an assay plate 161, tray 201, and lid 211. Assay plate 161 comprises a plurality of wells 163 and a water reservoir 162 along one or more (e.g., all four) edges of the plate. In some embodiments, the base of the assay plate 161 measures 85.49 mm by 127.77 mm. FIGS.

17A-D show various views of an array of wells 163 on assay plate 161. Wells 163 comprise holes 171 having a top surface 172 and bottom surface 173. In some embodiments, the holes 171 are approximately 1.6 mm in diameter. In some embodiments, the distance between holes 171 is approximately 4.5 mm. In some embodiments, the holes 171 comprise a plurality of upper plateau structures 174 on the top surface 172. In some embodiments, the holes 171 comprise a plurality of lower plateau structures 175 on the top surface 173. In some embodiments, the upper plateau structures 174 help to align apparatus for liquid handling with the holes 171 and/or prevent spreading of liquid from one well to another. In some embodiments, the lower plateau structures 175 substantially confine hanging drops to specific locations and geometries and/or prevent the spreading of hanging drops to neighboring wells.

In some embodiments, the upper plateau structures 174 and/or lower plateau structures 175 are manufactured using materials and/or processes substantially the same as the assay plate 161. In other embodiments, the upper plateau structures 174 and/or lower plateau structures 175 are manufactured using processes and/or materials substantially different from the assay plate 161. In some embodiments, the plateau structures are plastics created using 3D prototyping methods. In other embodiments, the plateau structures are printed structures of chemical entities, biological entities, or combinations thereof.

Figures 18, 19:
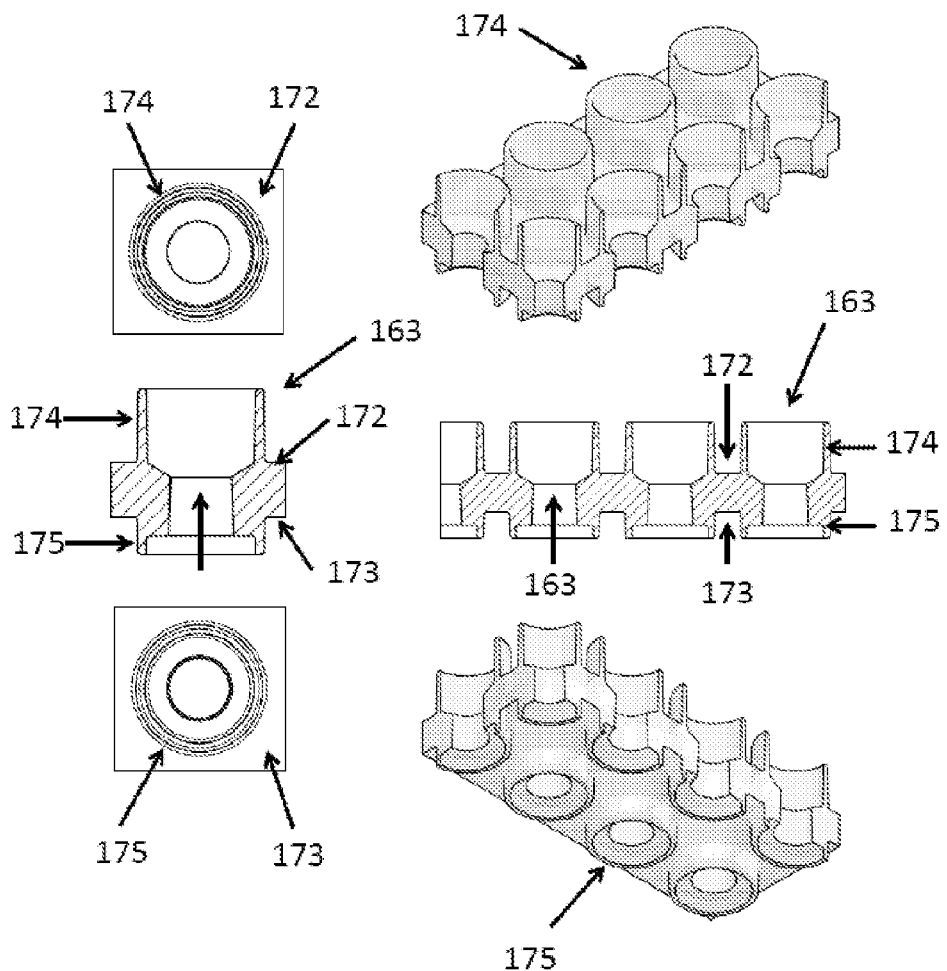
FIG. 18 shows a top, cross-sectional, and bottom view of an exemplary access hole structure, according to certain embodiments.
FIG. 19 shows cross section and isomeric 3D representations, from top and bottom, of an exemplary array of access holes, according to certain embodiments.
Figure 20:
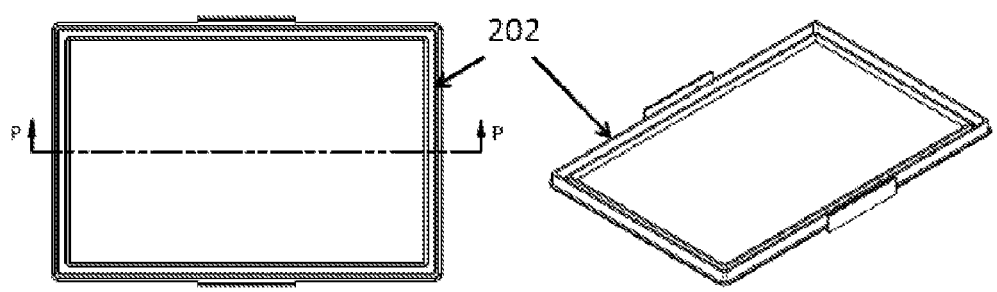
FIGS. 20 A-F illustrate an exemplary tray that the array plate shown in FIG. 16 may be used with, according to certain embodiments.
Figures 20A, 20B:
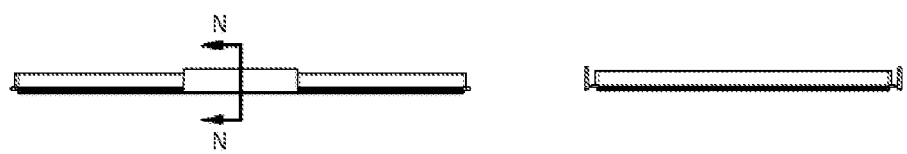
FIG. 20A shows a top view.
FIG. 20B shows an isomeric view from top.
Figures 20C, 20D:
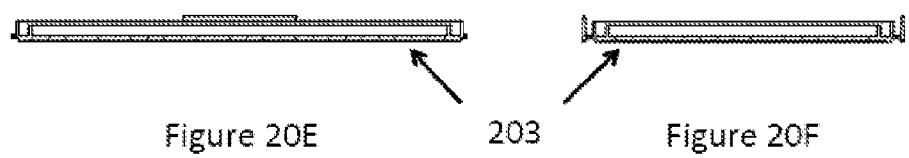
FIG. 20C shows a side view.
FIG. 20D shows an end view.

FIG. 18 shows the top, cross section, and bottom views of a single well 163. FIG. 19 shows the cross section view and 3D representations of an array of wells 163.

FIGS. 20A-F show various views of tray 201. FIGS. 21A-F show various views of lid 211. FIGS. 22A-F show various view of the assembly 221 formed by the assay plate 161, tray 201, and lid 211. The lid 211 covers and sits on top of the assay plate 161. The assay plate 161 sits on top of the tray 201. In some embodiments, assay plate 161 is substantially enclosed by tray 201 and lid 211.

In some embodiments, the tray comprises plate comprises a water reservoir 202 along one or more (e.g., all four) edges of the plate. In other embodiments, the water reservoir is in one or more other locations. In some embodiments, one or more water reservoirs are located at positions that provide an unobstructed view of wells 163 which make imaging and analysis easier. In certain embodiments, the tray 201 is substantially optically transparent, allowing convenient imaging and optical analysis of the hanging drops. In some embodiments, the reservoir contains aqueous fluids. In some embodiments, the water reservoir 202 substantially contributes to the maintenance of humidity. In other embodiments, the reservoir contains hydrogels, such as agarose gel, which is less prone to spill like aqueous fluids and can provide humidifying vapor. In other embodiments, the reservoir contains solids, for example, chemicals that vaporize as testing compounds.

In some embodiments, one or more of components of the assembly 221 are substantially optically transparent. In some embodiments, the assembly is sufficiently air tight to allow gas exchange between the interior and exterior of the assembly. In some embodiments, the assembly improves the preservation of humidity within the assembly. In some embodiments, the fit of components of the assembly is substantially tight, allowing the components to sit on one another securely during handling.

FIGS. 23A-B shows the side and front views of a stack of three assemblies 221. In some embodiments, the tray comprises structures 203 and the lid comprises structures 212 that allow the assemblies 221 to be substantially securely stacked on one another and remain so during handling.

FIGS. 24A-D shows exemplary variations of access hole structure, according to certain embodiments. Potential split lines for injection molding manufacturing are indicated by lines 241. Other location of the split lines are also contemplated. FIG. 24A shows an exemplary access hole structure with a tall and thin plateau structure on the top surface. FIG. 24B shows an exemplary access hole structure with a short and thin plateau structure on the top. FIG. 24C shows an exemplary access hole structure with a tall and thick plateau structure on the top. FIG. 24D shows an exemplary access hole structure with a tall and thin plateau structure on the top, with a different In some embodiments, access holes are in a multi-wall or multi-well type formation of rows and columns. In other embodiments, alternative geometric configurations are utilized (e.g., circular arrangements, irregular patterns, etc.). In some embodiments, access holes and plateaus may be of the same size, geometry and/or design on each plate. In some embodiments, access holes and plateaus are of substantially the same size, geometry and/or design on each plate. In other embodiments, size and/or shape of the access holes and plateaus may be varied. In some embodiments, access hole structure/geometry may be incorporated into other devices (e.g. analysis devices).

Devices may be constructed from suitable materials or combinations of materials. Examples include, but are not limited to, plastics (e.g., biocompatible plastics, polystyrene or other polymeric plastic), paper, metals, glass or combinations thereof. In some embodiments, injection molding is used to fabricate devices. In other embodiments, devices are fabricated using suitable methods or combinations of methods. Examples include, but are not limited to, molding (e.g. injection molding), rapid prototyping (e.g. stereolithography, 3D printing, selective laser sintering, fused deposition modeling, etc.), lithography (soft lithography), printing, or combinations thereof. In some embodiments, one or more parts of the devices are fabricated using substantially different materials and/or processes.

In some embodiments, plates are treated (e.g., in a chemical, physical, biological, texture manner) to, for example, control cell behavior, drop size, position, and geometry, etc. Methods for surface treatment include, but are not limited to, chemical modifications, physical modifications, plasma treatment, vapor deposition, adsorption and/or coating of chemical and/or biological entities, such as drugs, DNA, proteins, etc. and combinations thereof. In some embodiments, treatment is performed: to change the surface properties of the array plate, for example, hydrophobicity, protein attachment, chemical composition, biological composition, physical roughness, etc., or combinations thereof; to manipulate properties of the hanging drops, such as drop size, position, geometry, etc., or combinations thereof; and/or to control the behavior of cells, such as the rate of proliferation and/or differentiation, differentiation lineage, production of certain proteins and metabolites. In other embodiments, surface treatment is performed, for example by coating, to enable release and/or delivery of chemical and/or biological entities to the droplets and/or cells. In other embodiments, surface treatment is performed to produce a coating that detects changes in the properties of the drops and/or cells through mechanisms such as antibody and/or antigen binding. In other embodiments, the coating indicates the changes through alteration in optical, electrical, or other measureable properties of the coatings. For example, in some embodiments, devices are coated with a hydrophilic coating following fabrication, patterned, and the like.

In some embodiments, plates are sterilized prior to use or packaging. Sterilization is performed using any method suitable for the material of the plate and use (e.g., heat, high pressure, chemicals, irradiation or combinations thereof).

In some embodiments, the plate is integrated into a chamber/housing for controlling oxygen concentration, temperature, humidity, etc. (e.g., environmental control devices).

In some embodiment the maintenance of humidity may be improved. For example, both the array plate and/or the bottom plate may contain water reservoirs that help to humidify the atmosphere inside the enclosed system.

In some embodiments, the present disclosure provides systems and/or kits comprising devices (e.g., comprising assay plates, reservoirs, and covers), alone or in combination with reagents for culturing and characterizing cells using such devices (e.g., cells, buffers, growth media, test compounds, controls, etc.). In some embodiments, systems and kits comprise robotics for use in high throughput analysis (e.g., sample handling and analysis (e.g., plate readers) equipment).

II. Uses

The assay plate devices of certain embodiments of the present disclosure find use in a variety of applications. In some embodiments, the devices described herein are used in the culture of cells such as spheriods (e.g., cancer cell line spheriods) or other microorganisms or biomolecules. In some embodiments, spheriods are cultured in hanging drops as described herein. The cultured spheroids or other cells find use in a variety of research and screening applications.

Figure 10:
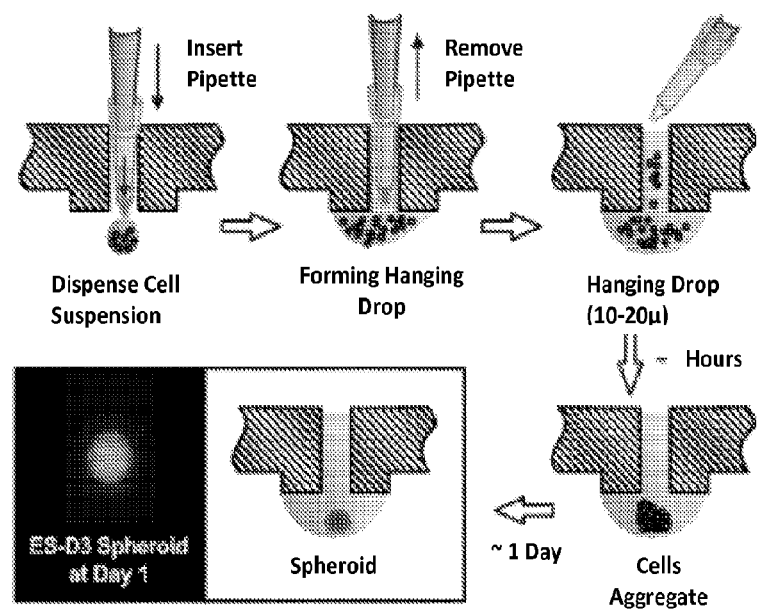
FIG. 10 shows a schematic of exemplary methods for adding and removing cells and liquids from devices of certain embodiments.
Figure 11:
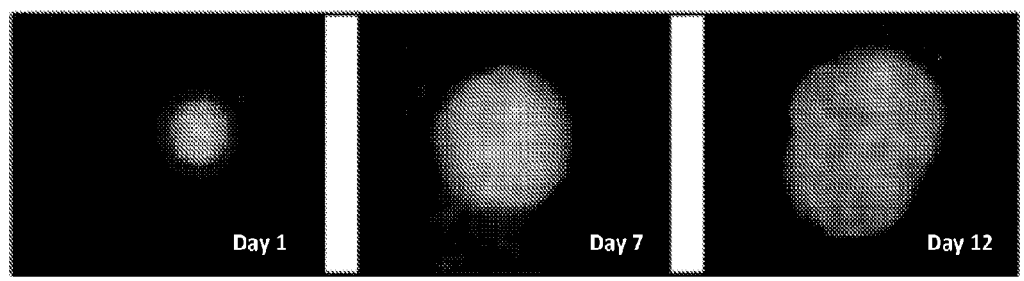
FIG. 11 shows mES spheroids cultured using methods of certain embodiments.
Figure 12:
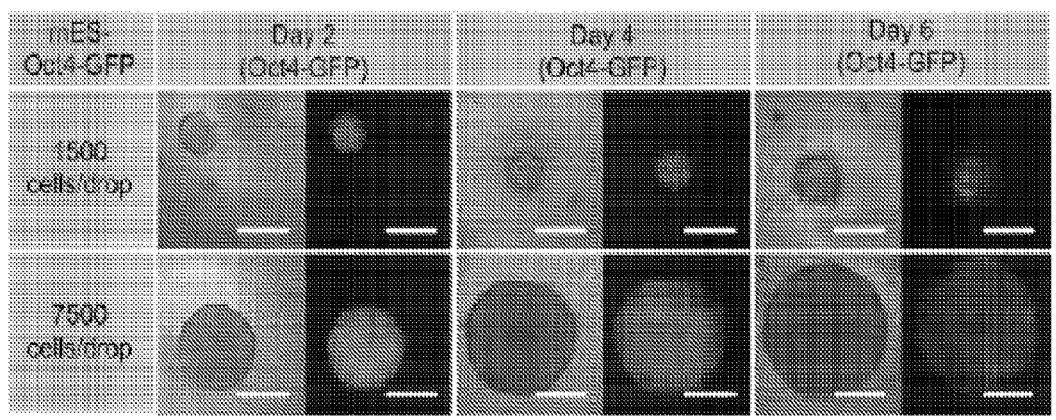
FIG. 12 shows mES spheroids cultured using methods of certain embodiments.
Figure 13:
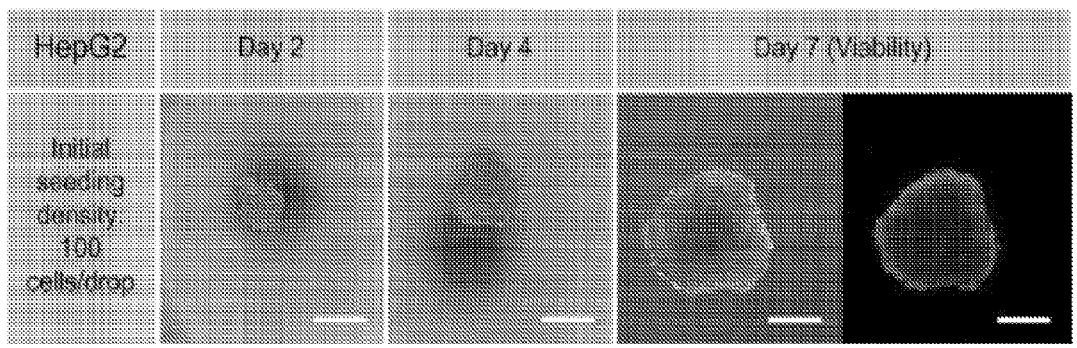
FIG. 13 shows hepatocyte spheroids cultured using methods of certain embodiments.

In some embodiments, to form hanging drops, a cell suspension solution is transferred (e.g., using a pipette) from the top side through the holes. In some embodiments, the end of the pipette tip or other liquid transfer device is inserted into the hole to guide the sample liquid to the bottom surface (See e.g., FIG. 10c). Once the droplet is formed on the lower surface, additional liquid addition (e.g., growth medium, test compounds, etc.) can be performed without the pipette tip or pin dispenser or other tool going through the hole but simply by touching the holes at the top surface. Because the lower droplet is larger, surface tension will cause fluid to flow from the top surface to the lower surface droplet. This allows minimal disturbance of the cells in the hanging drop during subsequent liquid handling. In some embodiments, media is exchanged and treatment of cells is performed via aspiration through the top of the plate or using capillary and/or microfluidic actions and/or devices.

The devices of certain embodiments of the present disclosure provide the advantage of allowing for control of time, spheroid size, spheroid composition (e.g., cell type(s), composition of cells, physical distribution of cells), treatment (e.g., test compound(s), schedule, duration, concentration), environment (e.g., temperature, oxygen concentration, humidity, etc.) or combinations thereof.

The liquid or cell samples can also be removed from the drop through the access holes using, for example, pipettes or slot pins (V&P Scientific, Inc., San Diego, Calif.). Also, in hanging drops, because there is no hard well bottom, but a droplet-air interface that changes positions depending on fluid volume, cells can be pipette out without concern of pipette tips crushing the cells or spheroids against a hard wall. Additional methods for removing cells from the drops include, but are not limited to, aspirating from the top of the plate, washing into a bottom plate, device or container, transferring into a bottom plate, device, container by touching the droplets, centrifuging into a bottom plate, device, container (e.g., an empty container or a container containing reagents or gel for further growth or differentiation or for collections for analysis) or transferring to another plate, device, container, etc. using capillary and/or microfluidic actions or combinations thereof.

The size of the hanging drop is confined, at least in part, by the diameter of the plateau on the bottom surface. As a result, the geometry of the hanging drop is kept consistent, or substantially consistent, during the culturing process without spreading, which leads to more robust and stable culturing conditions not possible on conventional flat hanging drop substrates. Conventional hanging drop methods involve inverting the lid of a Petri dish or culture plate following dispensing of drops on the inside of the lid. The movement of inverting the lid and the lack of physical structures that confine each drop can lead to spreading, fusing, falling, and other alterations of the drops, resulting in variability in the size, geometry, viability, and other measurable qualities of the spheroids in the drops.

The devices of embodiments of the present disclosure find uses in a variety of research, clinical and screening applications. Examples include, but are not limited to, formation of cellular aggregates for research, drug discovery and toxicity testing; culture of embryos, tissue slices, small organisms, and worms (e.g., *C. elegans*); bacteria culture (minimal contact with surface prevents biofilm formation and increases gas exchange, which is important for many types of bacteria); environmental monitoring; toxicology studies of gaseous substances; water quality testing; germination of seeds; self-assembly of biological and chemical entities, such as, for example, cells, nanoparticles, proteins, peptides, DNAs, etc.; crystallization of chemical species; concentration of aqueous solutions through gradual evaporation, imaging (e.g., imaging of the above mentioned processes); in vitro biochemical assays (e.g., enzyme assays and assay of receptor, protein-protein interactions); measurement (e.g., colorimetric, fluorescence, luminescence, radiometric, etc.); cell seeding and the like or combinations thereof. Certain exemplary applications are described herein.

In some embodiments, devices are used in cell seeding applications. In some embodiments, cells are seeded in aqueous media/reagents or gel. In some embodiments, cells are seeded with chemical, biomolecules, and/or particles (e.g., nanoparticles, microspheres, etc.). In some embodiments, cells are seeded as a dispersion or individual single cells or cellular aggregates. The present disclosure is not limited a particular source of cells. In some embodiments, cells are of various origin (e.g., human, rat, mouse, etc.) and different forms (e.g., primary cells, cell lines, stem cells, induced pluripotent stem cells, etc.) may be used. In some embodiments, multiple cell types are seeded to achieve co-culture of cells (e.g., a mixture of multiple cell types seeded at once or single and/or mixture of multiple cell types seeded in sequential manner). In some embodiments, cells that are alive, growing, dormant or chemically processed (e.g., fixed by chemical fixatives) may be used.

In some embodiments, cells or spheroids cultured using the devices and methods of the present disclosure find use in drug screening applications. For example, in some embodiments, cultured cancer cell line spheroids or other cells are contacted with an anticancer or other test drug. In some embodiments, test compounds or conditions such as chemicals, vapors (e.g., naphthalene), biomolecules or nanoparticles (e.g., alone or conjugated to a drug) may be used. The viability of the cells is then monitored (e.g., using a dye that stains for viability and a plate reader).

In some embodiments, the devices may be used in the maintenance of stem cells (e.g., cancer stem cells). In some embodiments, cancer stem cells may be co-cultured with spheroids to mimic the in vivo environment of a tumor. Cancer stem cells cultured using such methods find use in research and drug screening applications.

The use of array devices, according to certain embodiments, allows for high throughput screening and research applications. In some embodiments, devices may comprise one or more 96, 384 or other size well arrays. The use of standard sized arrays allows for the use of existing robotic equipment (e.g., commercially available equipment such as liquid handling and plate readers) for high throughput screening applications. Certain device embodiments of the present disclosure are also amenable to stacking.

EXPERIMENTAL

The following examples are provided in order to demonstrate and further illustrate certain preferred embodiments and aspects of the present disclosure and are not to be construed as limiting the scope thereof.

Example 1

A. Methods
Device Design:

A spheroid culture device based on hanging drop cell culture technique is shown in FIG. 1a. The device is fabricated by injection molding using polystyrene resin. In order to overcome a drawback in liquid handling of the hanging drop method, each cell culture site was composed of an access hole through the substrate with a plateau on the bottom surface. These cell culture sites were arranged in 384-well plate format (16 rows, 24 columns, and 4.5 mm apart in both directions as shown in FIGS. 1b and c)), which enables use of commercially available high throughput screening instruments (e.g. fluid manipulation robots and plate readers) that are commonly utilized in biomedical laboratories. In addition, the plate dimension was also designed to be identical with general 384-well plates, and can be stacked with other well plates. To alleviate the commonly encountered evaporation problem due to the small volume of the hanging drops (tens of µl), a water reservoir was constructed around the peripheral of the culture sites.

Prior to usage of the plate, a hydrophilic coating (Pluronic F108, 0.1%) was applied onto the entire device surface for an hour. The plate was then washed using distilled water, blow-dried using nitrogen gas, and sterilized by exposing to UV light for a half hour. To form hanging drops, cell suspension solution was pipetted through the access holes using either a single- or multi-channel pipette or an automated liquid handling robot. Note that the end of each pipette tip is inserted into the access hole to guide the sample liquid to the bottom surface. The liquid or the cell samples can also be removed from the drop through the access holes using pipettes or slot pin replicators (V&P Scientific, Inc.). Consequently, the entire sample handling processes can be accomplished from the top surface of the plate, which avoids tedious petri-dish inversion used in conventional hanging drop methods. Furthermore, this liquid handling scheme makes the device fully compatible to automated high-throughput screening instruments, and makes scale up of spheroid experiments feasible. In addition, the size of the hanging drop was confined by the diameter of the plateau on the bottom surface. As a result, the geometry of the hanging drop can be kept consistent along the culturing process without spreading, which leads to more robust and stable culturing conditions.

Methods:

To investigate the stability of long-term hanging drop spheroid culture using the designed array plate, osmolality measurements were performed while culturing three types of cells: kidney fibroblast cell (COS7), murine embryonic stem (mES) cell (ES-D3), and a human carcinoma cell that stably express mesothelin (A431.H9). Prior to performing hanging drop culture using the plate, ES-D3 cells were cultured in dishes coated with 0.1% w/v porcine gel (Sigma-Aldrich) and maintained in medium consisting of Dulbecco's Modified Eagle's Medium (DMEM) (Gibco 11960, Invitrogen) with 15% v/v fetal bovine serum (FBS) (Gibco 10082, Invitrogen), 4 mM L-glutamin (Invitrogen), 0.1 mM 2-mercapto-ethanol (Sigma-Aldrich), 0.02% v/v sodium pyruvate (Sigma-Aldrich), 100 U ml$^{-1}$ penicillin (Invitrogen), 100 U ml$^{-1}$ streptomycin (Invitrogen), and 1000 U ml$^{-1}$ ESGRO (Invitrogen) which contains leukemia inhibitory factor (LIF). COS7 and A431.H9 cells were cultured in DMEM (Gibco 11965, Invitrogen) with 10% v/v FBS (Gibco 10082, Invitrogen), and 1% v/v antibiotic-antimicotic (Gibco 15240, Invitrogen). All the cells were cultured in a humidified incubator (37° C. in an atmosphere of 5% $CO^2$). Cell suspensions for the hanging drop experiments were made by dissociating cells with 0.25% trypsin-EDTA (Gibco 25200, Invitrogen), centrifugation of dissociated cells at 1000 rpm for 1 min at room temperature, and re-suspended in growth media. Cell density was estimated using a hemocytometer.

On the spheroid culture plate, a 15 µl cell suspension was dispensed into the access hole at each cell culture site to form a hanging drop. In order to prevent evaporation, 4 ml of distilled water was added into the peripheral water reservoir. In addition, the plate was sandwiched by a well-plate lid and a 96-well plate filled with distilled water, and wrapped using a Parafilm. The growth media was exchanged every other day by taking 5 µl solution from a drop, and adding 7 µl fresh growth media into a drop. For the osmolality measurement, 10 µl sample solution was pipetted out from a drop and transferred to a vapor pressure osmometer (Vapro Model 5520, Wesco, Inc.) for analysis.

For demonstration of anti-cancer drug sensitivity testing, A431.H9 spheroids at three different sizes (300, 1500, and 7500-cell spheroids) were tested under the effect of two types of drug—tirapazamine (TPZ) (Toronto Research Chemicals) and 5-fluorouracil (5-FU) (Sigma-Aldrich). According to the procedure mentioned above, A431.H9 spheroids at the specified cell numbers were formed, and their growth media were exchanged every other day. TPZ and 5-FU stock solutions of four times the final testing concentrations (0, 0.1, 1, 10, 100, 1000, 5000 µM) were initially prepared in Dulbecco's phosphate buffered saline (D-PBS) (Gibco 14190, Invitrogen). On day 2 of A431.H9 spheroid culture, 5 µl of the appropriate concentration of TPZ (or 5-FU) stock solutions was subsequently added to each of the 15 µl A431.H9 cell hanging drop droplets. Cellular viability was monitored at 24, 48, 72, and 96 hours of drug incubation using alamarBlue (Invitrogen). Following manufacturer's protocol, 2 µl (one-tenth of each hanging drop sample volume) of alamarBlue was added to each A431.H9 hanging drop spheroid sample and incubated for 2 hours. Following incubation, each A431.H9 hanging drop spheroid sample plate was read using a plate reader (FLx800 Fluorescence Microplate Reader, Biotek) at 525 nm excitation and 590 nm emission to obtain fluorescence intensity readout. As the fluorescence intensity of alamarBlue is directly proportional to cell number, the average percent cell viability for each drug concentration can be calculated easily by normalizing to the 0 µM untreated spheroid control. Anti-cancer drug sensitivity experiments under 2D control conditions were performed in standard tissue culture treated 96-well plates (Corning Costar 3596), with everything else being the same as the 3D spheroid experiments. 50% of culture media was replaced by fresh media every other day.

B. Results

A schematic of the 384 hanging drop array plate is shown in FIG. 1a and a picture of the plate containing 192 hanging drops arranged in an alternating fashion is shown in FIG. 1b. The hanging drop spheroid culture sites were arranged in the standardized 384-well plate format with 16 rows and 24 columns separated by 4.5 mm apart in both directions. A water reservoir designed in the outer ring of the plate further holds up to 4 mL of water to alleviate evaporation. The enlarged cartoon in FIG. 1a further shows the access hole on the top surface of the plate with a liquid droplet hanging and confined by the diameter of the plateau on the bottom surface. Such a custom made polystyrene plate allows efficient formation of hanging drops in a high-throughput array format. FIG. 1c is a snapshot of the hanging drop formation process in the 384 hanging drop array plate by a commercially available liquid handler (CyBi-Well), indicating the utility of scaling up hanging drop spheroid culture using this plate in a high-throughput manner.

FIG. 2a shows a plot of the average osmolality of the COS7, mES, and A431.H9 cell culture media vs. time over a period of 5 days. With ~50% exchange of culture media ever other day, the osmolality of the cell culture media is relatively stable over a 2 week period. FIG. 2b shows the live/dead images of the COS7 and mES cell spheroids. It indicates that most cells were still alive after 12 days of culture. FIG. 2c shows the relationship between A431.H9 spheroid size (diameter) and cell number. To investigate whether spheroids cultured in the 384 hanging drop array plates were growing properly, spheroid size was monitored every day. FIG. 2c also shows the average A431.H9 spheroid size over a 1 week period. The plot clearly shows that A431.H9 spheroids at various different sizes are still proliferating over the 7-day culture period. The stability of the culture media osmolality together with proper spheroid growth indicate that the 384 hanging drop array plate offers a suitable environment for spheroid culture. The stability of the hanging drop culture condition along with the robustness of the hanging drop geometry without spreading out allows for easy long-term spheroid culture.

Figure 3:
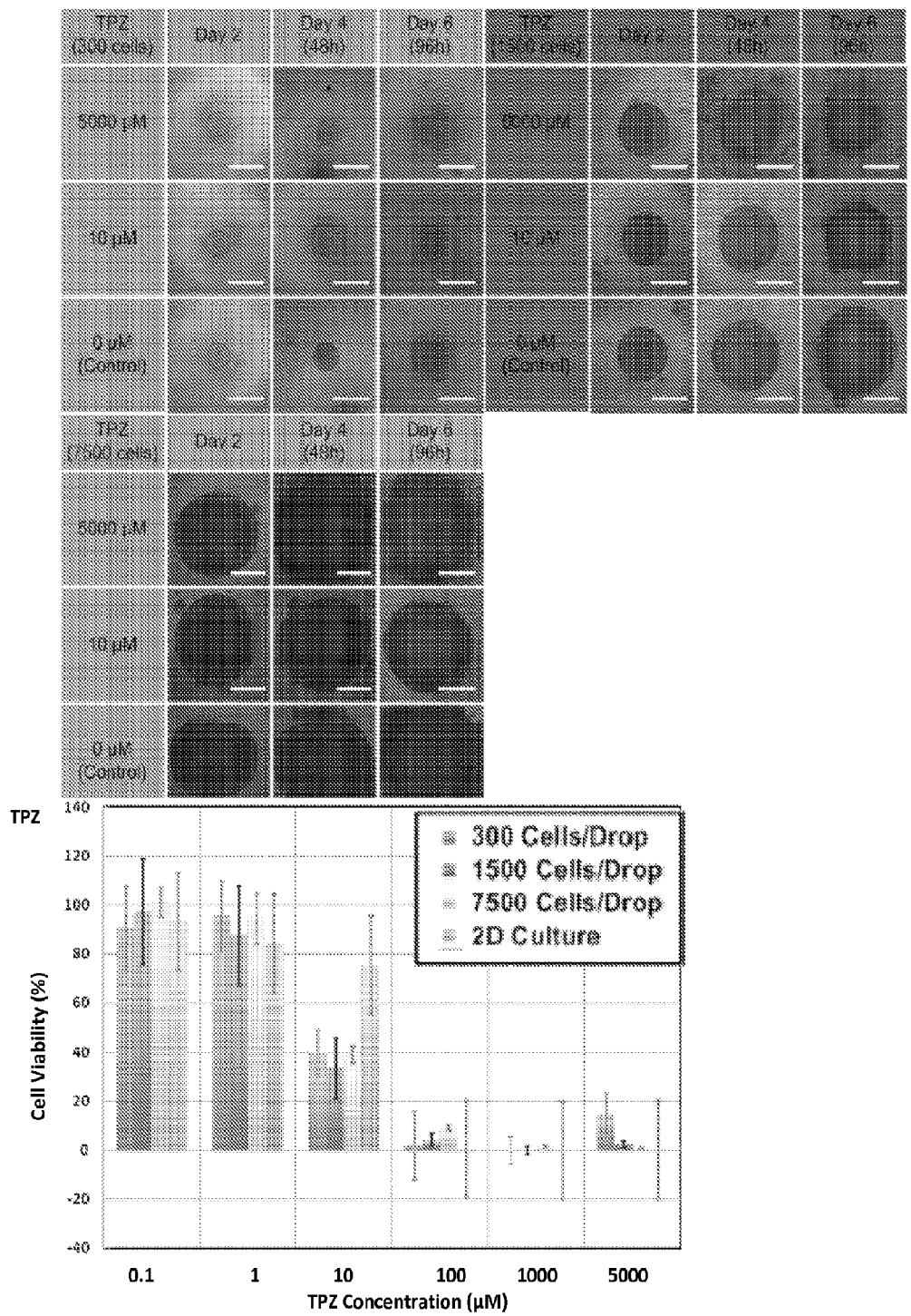
FIG. 3 shows TPZ results, time-lapse images of A431.H9 spheroids at various concentrations, bar graph outlining percent of control cell viability at various concentrations for all spheroid sizes and conventional 2D culture condition 96 h after drug treatment, according to certain embodiments.

As a demonstration of anti-cancer drug sensitivity testing in the 384 hanging drop array plates, two anti-cancer drugs were tested—TPZ and 5-FU. FIGS. 3a-c show the time-lapse images of A431.H9 spheroids treated with TPZ at 0, 10, and 5000 µM for 3 different spheroid sizes (300, 1500, and 7500-cell spheroids). The control untreated A431.H9 spheroids at all 3 sizes still grow and proliferate properly over the duration of drug treatment. On the other hand, the size of A431.H9 spheroids treated with 10 µM of TPZ for all 3 spheroid sizes stayed relatively constant over the drug treatment period, indicating inhibition of spheroid growth. Finally, A431.H9 spheroids treated with 5000 µM of TPZ for all 3 sizes increasingly were exhibited poor viability over the 96 hours of drug treatment, indicating drug cytotoxicity. FIG. 3d shows the bar graph outlining the % cell viability at various TPZ concentrations 96 hours after initial drug treatment for all 3 A431.H9 spheroid sizes and conventional 2D culture condition. The $IC_{50}$ of A431.H9 cells cultured in conventional 2D condition is about 50 µM, while the $IC_{50}$ of the A431.H9 3D spheroids for all 3 sizes is about 8 µM. Contrary to most anti-cancer drugs, A431.H9 cells treated with TPZ are more resistant when cultured under 2D conditions rather than 3D conditions.

Similarly, FIGS. 4a-c show the time-lapse images of A431.H9 spheroids treated with 5-FU at 0, 10, and 5000 µM for 3 different spheroid sizes (300, 1500, and 7500-cell spheroids). Again, the control untreated A431.H9 spheroids at all 3 sizes all look healthy and still proliferate properly over the duration of drug treatment. However, when A431.H9 spheroids were treated with 10 µM of 5-FU, the A431.H9 spheroids slowly become smaller over the 96 hours of drug treatment for all 3 sizes, indicating inhibition of spheroid growth. Finally, when A431.H9 spheroids were treated with 5000 µM of 5-FU, spheroid integrity was greatly compromised with cells started to dissociate at 48 hours after drug treatment for all 3 sizes. By 96 hours after drug treatment, significant portions of cells had already dissociated from the A431.H9 spheroids, indicating drug cytotoxicity. FIG. 4d summarizes the results with the 5-FU bar graph outlining the % cell viability at various concentrations 96 hours after treatment for all 3 A431.H9 spheroid sizes and traditional 2D culture condition. The $IC_{50}$ of A431.H9 cells cultured in traditional 2D condition is about 0.1 µM, while the $IC_{50}$ of the A431.H9 3D spheroids is about 3, 1, and 90 µM for 300, 1500, and 7500-cell spheroids, respectively. As expected in most anti-cancer drugs, A431.H9 cells treated with 5-FU are more resistant when cultured under 3D condition than the traditional 2D culture.

Example 2

Additional Plate Design

Figure 14B:
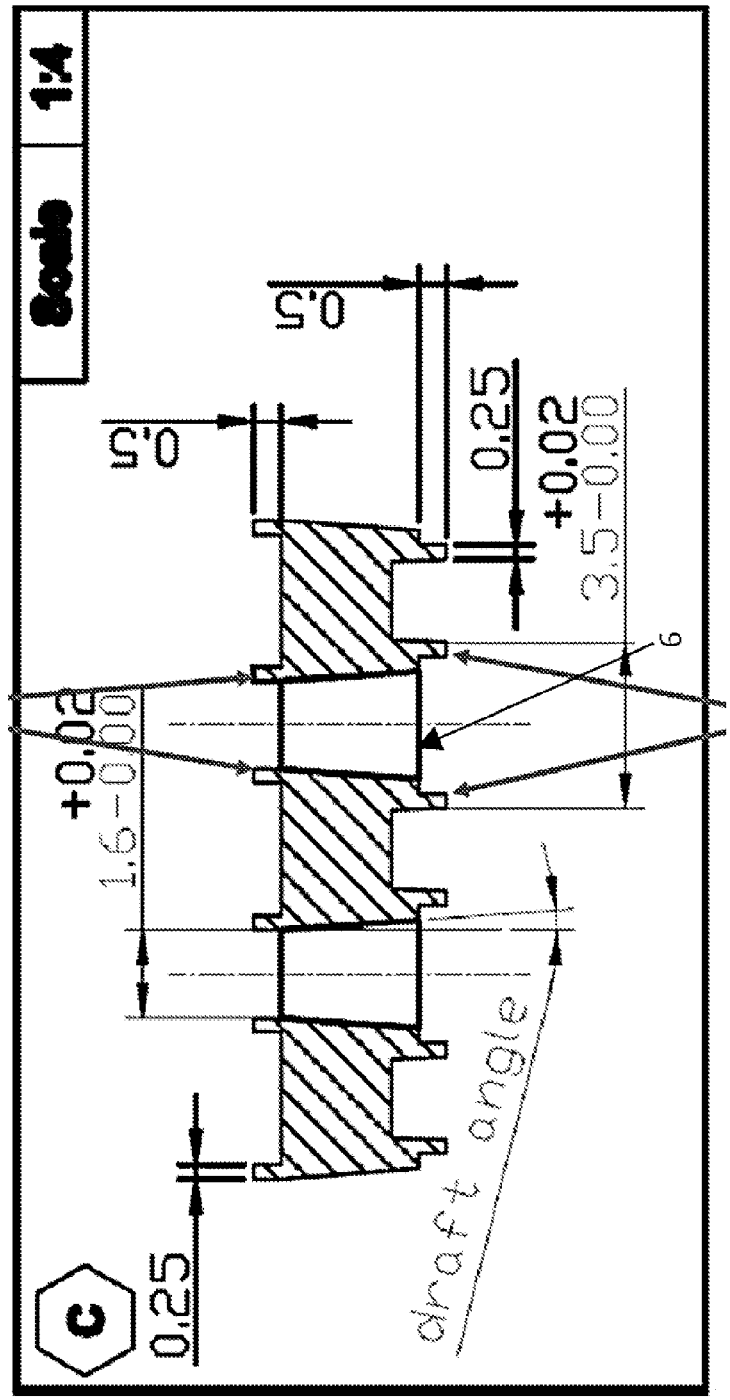

The devices of certain embodiments of the present disclosure are able to robustly generate hanging drops, maintain hanging drops, provide the ability to add and/or remove fluid from the hanging drops, or combinations thereof. Because each access hole is configured to hold a hanging drop securely in place, large numbers of hanging drops can be formed reproducibly. In certain embodiments, each access hole is substantially identical. The access holes which have openings on the top surface of the array plate allow fluids to be withdrawn or added to form hanging drops or to already formed hanging drops. This means fluids can be withdrawn or added throughout an experiment to manipulate and/or maintain measurable properties of the hanging drops and/or the contents in said hanging drops. This example describes a device (for example as described in FIG. 14) that provides an extra topographical barrier to confine the droplets stably. The barrier is shown in FIG. 14B. The device includes an additional ring (0.25 µM wide and 0.5 µM in height measured from the plate top surface or the bottom of the plateau) on both the top and bottom of the hole. The barrier may be utilized for stabilization of droplets in through holes where the ring is not on a surface but on the edges of a hole where liquid can move up and down through the hole.

The performance of the device was assayed using Z-factor analysis. The Z-factor is an assay performance measure used to optimize dynamic range of signal response and its variability in screening assays. Typically when the Z-factor is greater than 0.5, the assay is considered "excellent." However, in certain applications a lower Z-factor may be sufficient.

Calculating Z-factors for fluorescence-based assays and absorbance-based assays in 384 hanging drop plates and standard 384-well plates was performed as follows: A range of fluorescein or yellow food color concentrations were placed in the 384 hanging drop plates as well as standard 384-well plates. A plate reader was used to measure the readings. Z-factors were calculated based on the values obtained at each concentration for each type of plate. Results are shown in FIG. 15. For most concentrations, the z-factors are above 0.5. 384 hanging drop plate Z-factors are comparable to the standard 384-well plate.

Example 3

This Example provides examples of methods, systems and devices that further illustrate certain non-limiting embodiments of the present disclosure:

Example 1: A system, comprising
   a) at least one array plate, the at least one array plate comprising a top surface and a bottom surface and a plurality of holes therein, wherein each of the plurality of holes comprises a top and a bottom and wherein the bottom surface of said array plate comprises a at least one plateau substantially adjacent to the bottom of at least one of the plurality of holes; and
   b) wherein the at least one array plate is configured to accommodate a plurality of hanging drops, wherein each drop hangs from a corresponding one of the plurality of said holes and extends beneath the hole, wherein the number of hanging drops the that at least one array plate can accommodate is equal to or less than the number of holes in the at least one array plate.

2. The system of example 1, further comprising at least one second plate positioned below said at least one array plate.
3. The system of examples 1 or 2, wherein said at least one array plate further comprises at least one reservoir.
4. The system of examples 1, 2 or 3, wherein said at least one second plate further comprises at least one reservoir.
5. The system of examples 1-3 or 4, wherein both the at least one array plate and the at least one second plated both contain at least one reservoir.
6. The system of examples 1-4 or 5, comprising one or more of the following: one or more reservoirs within the at least one array plate; one or more reservoirs with the at least one second plate; one or more reservoirs within the at least one array plate wherein the at least one second plate has no reservoir; one or more reservoirs within the second plated positioned wherein the at least one array plate has no reservoir; or one or more reservoirs within both the at least one array plate and the at least one second plate.
7. The system of examples 1-5 or 6, wherein each drop hangs from a corresponding one of the plurality of said holes and extends beneath the hole.
8. The system of examples 1-6 or 7, wherein said at least one second plate contacts at least a portion of the edges of said at least one array plate, and wherein said at least one second plate does not substantially contact one or more of said hanging drops.
9. The system of examples 1-7 or 8, further comprising at least one lid for said at least one array plate, wherein said at least one lid is placed on top of one or more said at least one array plate and wherein said at least one lid does not contact the portion of the plurality of holes configured to accommodate the plurality of hanging drops.
10. The system of examples 1-8 or 9 wherein said one or more reservoirs further contains one or more substances.
11. The system of examples 1-9 or 10, wherein one or more of the plurality of hanging drops contains one or more of the following: a plurality of cells; at least one complex tissue or organisms; an aqueous fluid containing biological and/or chemical entities; one or more proteins; one or more nanoparticles, one or more test compounds; one or more drugs; solid or gel formed by aqueous liquid; or combinations thereof.
12. The system of examples 1-10 or 11, wherein said holes are approximately 1.6 mm in diameter.
13. The system of examples 1-11 or 12, wherein said holes are approximately 4.5 mm apart.
14. The system of examples 1-12 or 13, wherein said array plates comprises a plurality of rows and columns of said holes therein.
15. The system of examples 1-10, or 11 wherein the edge of said at least one plateau comprises at least one ring structure.
16. The system of examples 1-14 or 16, wherein the at least one array plate is treated in order to modify properties of the at least one array plate.
17. The system of examples 1-15 or 16, wherein the at least one array plate is treated in order to modify the physical, chemical and/or biological properties of the at least one array plate.
18. The system of examples 1-16 or 17, wherein one or more of the at least one array plate, the at least one second plate, and/or the at least one lid is treated in order to modify to properties of the corresponding treated surface.
19. The system of examples 1-17 or 18, wherein the at least one array plate, the at least one second plate, and/or the at least one lid is treated in order to modify the physical, chemical and/or biological properties of the corresponding surface treated.
20. The system of examples 1-18 or 19, wherein said top surface of said at least one array plate comprises at least one second plateau substantially adjacent, or adjacent, to the top surface of one or more of said holes therein.
21. The system of examples 1-19 or 20, wherein the system complies with American National Standards Institute and/or Society for Biomolecular Sciences standards.
22. The system of examples 1-20 or 21, wherein one or more of the at least one assay plate, the at least one second plate, and the at least one lid is optically transparent and provides a substantially unobstructed view for optical imaging and/or analysis.
23. The system of examples 1-21 or 22, wherein said system is compatible with high-throughput screening.
24. The system of examples 1-22 or 23, wherein said systems are stackable.
25. The system of examples 1-23 or 24, wherein the at least one plateau on the bottom surface of the at least one array plate is configured to stabilize a geometry of said plurality of hanging drops.
26. The system of examples 1-24 or 25, wherein the at least on plateau on the bottom surface of the at least one array plate is configured to stabilize a position of said plurality of hanging drops.
27. The system of examples 1-25 or 26, wherein the at least one array plate is configured to stabilize and maintain measurable properties of said plurality of hanging drops.
28. The system of examples 1-26 or 27, wherein the at least one array plate further comprises at least one plateau on the top surface substantially adjacent to the top of at least one of the plurality of holes.
29. The system of examples 1-27 or 28, wherein the at least one array plate further comprises at least one plateau on the top surface substantially adjacent to the top of at least one of the plurality of holes, wherein said at least one plateau on the top surface of said at least one array plate is configured to improve a transfer of liquids in and/or out of the holes.
30. The system of examples 1-28 or 29, wherein the system is configured to maintain a substantially stable humidity.

31. The system of examples 1-29 or 30, wherein the system is configured to maintain measurable properties of the environment of the plurality of hanging drops.

32. The system of examples 1-30 or 31, wherein the system is configured to handle small volumes of fluid.

33. The systems of examples 1-31 or 32, wherein the system is configured to permit long terms culturing of a plurality of cells within the one or more plurality of hanging drops.

34. The systems of examples 1-32 or 33, wherein the system is configured to permit one or more of the following: long terms culturing, maintaining, analysis and/or testing of a plurality of cells; long term culturing, maintaining, analysis and/or testing of at least one complex tissue or organisms; long term culturing, maintaining, analysis and/or testing of an aqueous fluid containing biological and/or chemical entities; long term culturing, maintaining, analysis and/or testing of one or more proteins; long term culturing, maintaining, testing and or analysis of one or more nanoparticles; long term culturing, maintaining, analysis and/or testing of one or more test compounds; long term culturing, maintaining, analysis and or testing of one or more drugs; or combinations thereof.

35. The system of examples 1-33 or 34, wherein said plurality cells are growing in a spheroid.

36. The system of examples 1-34 or 35, wherein said system further comprises one or more high throughput sample handling devices selected from the group consisting of robotic sample handling devices and plate readers.

37. Any method using one or more of systems of examples 1-35 or 36.

38. A method, comprising: inserting a plurality of hanging drops into a system, comprising:
a) at least one array plate, the at least one array plate comprising a top surface and a bottom surface and a plurality of holes therein, wherein each of the plurality of holes comprises a top and a bottom and wherein the bottom surface of said array plate comprises a at least one plateau substantially adjacent to the bottom of at least one of the plurality of holes; and
b) wherein the at least one array plate is configured to accommodate a plurality of hanging drops, wherein each drop hangs from a corresponding one of the plurality of said holes and extends beneath the hole, wherein the number of hanging drops the that at least one array plate can accommodate is equal to or less than the number of holes in the at least one array plate; and
performing on one or more of the hanging drops culturing, maintaining, analysis, testing, or combinations thereof.

39. The method of example 38, wherein said each drop is inserted from the top side or the bottom side of said at least one said array plate through said hole.

40. The method of examples 38 or 39, further comprising the step of removing said hanging drop through said holes.

41. The method of examples 38, 39 or 40, further comprising the step of removing or adding fluid to at least one or more hanging drops.

42. The method of examples 38-40 or 41, further comprising at least one second plate positioned below said at least one array plate.

43. The method of examples 38-41 or 42, wherein said at least one array plate further comprises at least one reservoir.

44. The method of examples 38-42 or 43, wherein said at least one second plate further comprises at least one reservoir.

45. The method of examples 38-43 or 44, wherein both the at least one array plate and the at least one second plated both contain at least one reservoir.

46. The method of examples 38-44 or 45, wherein each drop hangs from a corresponding one of the plurality of said holes and extends beneath the hole.

47. The method of examples 38-45 or 46, wherein one or more of the plurality of hanging drops contains one or more of the following: a plurality of cells; at least one complex tissue or organisms; an aqueous fluid containing biological and/or chemical entities; one or more proteins; one or more nanoparticles, one or more test compounds; one or more drugs; or combinations thereof.

48. The method of examples 38-46 or 47, wherein one or more of the at least one array plate, the at least one second plate, and/or the at least one lid is treated in order to modify to properties of the corresponding treated surface.

49. The method of examples 38-47 or 48, wherein the at least one array plate, the at least one second plate, and/or the at least one lid is treated in order to modify the physical, chemical and/or biological properties of the corresponding surface treated.

50. The method of examples 38-48 or 49, wherein said top surface of said at least one array plate comprises at least one second plateau substantially adjacent, or adjacent, to the top surface of one or more of said holes therein.

51. The method of examples 38-49 or 50, wherein the method complies with American National Standards Institute and/or Society for Biomolecular Sciences standards.

52. The method of examples 38-50 or 51, wherein one or more of the at least one assay plate, the at least one second plate, and the at least one lid is optically transparent and provides a substantially unobstructed view for optical imaging and/or analysis.

53. The method of examples 38-51 or 52, wherein said method is compatible with high-throughput screening.

54. The method of examples 38-52 or 53, wherein said systems are stackable.

55. The method of examples 38-53 or 54, wherein the at least one plateau on the bottom surface of the at least one array plate is configured to stabilize a geometry of said plurality of hanging drops.

56. The method of examples 38-54 or 55, wherein the at least on plateau on the bottom surface of the at least one array plate is configured to stabilize a position of said plurality of hanging drops.

57. The method of examples 38-55 or 56, wherein the at least one array plate is configured to stabilize and maintain measurable properties of said plurality of hanging drops.

58. The method of examples 38-56 or 57, wherein the at least one array plate further comprises at least one plateau on the top surface substantially adjacent to the top of at least one of the plurality of holes.

59. The method of examples 38-57 or 58, wherein the at least one array plate further comprises at least one plateau on the top surface substantially adjacent to the top of at least one of the plurality of holes, wherein said at least one plateau on the top surface of said at least one array plate is configured to improve a transfer of liquids in and/or out of the holes.

60. The method of examples 38-58 or 59, wherein the method is configured to maintain a substantially stable humidity.

61. The method of examples 38-59 or 60, wherein the method is configured to maintain measurable properties of the environment of the plurality of hanging drops.

62. The method of examples 38-60 or 61, wherein the method is configured to handle small volumes of fluid.

63. The methods of examples 38-61 or 62, wherein the method is configured to permit long terms culturing of a plurality of cells within the one or more plurality of hanging drops.

64. The methods of examples 38-62 or 63, wherein the method is configured to permit one or more of the following: long terms culturing, maintaining, analysis and/or testing of a plurality of cells; long term culturing, maintaining, analysis and/or testing of at least one complex tissue or organisms; long term culturing, maintaining, analysis and/or testing of an aqueous fluid containing biological and/or chemical entities; long term culturing, maintaining, analysis and/or testing of one or more proteins; long term culturing, maintaining, testing and or analysis of one or more nanoparticles; long term culturing, maintaining, analysis and/or testing of one or more test compounds; long term culturing, maintaining, analysis and or testing of one or more drugs; or combinations thereof.

65. The method of examples 38-63 or 64, wherein said method further comprises one or more high throughput sample handling devices selected from the group consisting of robotic sample handling devices and plate readers.

The following additional examples further illustrate certain non-limiting device embodiments of the present disclosure:

Device Example 1. A device, comprising:
an array plate, comprising a top surface and a bottom surface, wherein said array plate comprises a plurality of holes therein, wherein each hole comprises a top surface and a bottom surface and wherein the bottom surface of said array plate comprises at least one plateau either adjacent, or substantially adjacent, to the bottom surface of one or more of said holes.

2. The device of example 1, wherein said device further comprises a reservoir.
plate, wherein said reservoir plate substantially contacts the edges of said array plate, and wherein said reservoir plate does not substantially contact one or more of said holes.

3. The device of examples 1 or 2, wherein said reservoir plate contacts only the edges of said array plate.

4. The device of examples 1, 2, or 3 further comprising a cover for said array plate, wherein said cover is placed on top of said array plate and wherein said cover does not substantially contact one or more of said holes.

5. The device of examples 1-3, or 4 wherein said reservoir further comprises a humidifying substance.

6. The device of examples 1-4, or 5 wherein said reservoir plate is located substantially below said array plate.

7. The device of examples 1-5 or 6, wherein said reservoir plate does not contact said plurality of holes of said array plate.

8. The device of examples 1-6, or 7 wherein said array plate comprise 384 holes.

9. The device of examples 1-7, or 8 wherein said holes are approximately 1.6 mm in diameter.

10. The device of examples 1-8, or 9 wherein said holes are approximately 4.5 mm apart.

11. The device of examples 1-9, or 10, wherein said array plates comprises a plurality of rows and columns of said holes therein.

12. The device of examples 1-10, or 11 wherein the edge of said at least one plateau comprises at least one ring structure.

13. The device of examples 1-11, or 12 wherein the bottom surface of said array plate is coated with at least one surface treatment material.

14. The device of examples 1-12 or 13, wherein said top surface of said array plate comprises at least one second plateau substantially adjacent to the top surface of one or more of said holes therein.

15. The device of examples 1-13 or 14, wherein the device complies with American National Standards Institute and/or Society for Biomolecular Sciences standards.

16. The device of examples 1-14 or 15, wherein said reservoir plate further comprises a bottom surface portion that is optically transparent and provides a substantially unobstructed view for optical imaging and/or analysis.

17. The device of examples 1-15 or 16, wherein said device is compatible with high-throughput screening.

18. The device of examples 1-16 or 17, wherein a plurality of said devices are stackable.

All publications and patents mentioned in the above specification are herein incorporated by reference in their entirety. Various modifications and variations of the described devices, methods and/or systems will be apparent to those skilled in the art without departing from the scope and spirit of the disclosure. Although the inventions have been described in connection with specific preferred embodiments, it should be understood that the inventions as claimed should not be unduly limited to such specific embodiments. Indeed, various modifications of the described modes for carrying out the inventions which are obvious to those skilled in the relevant fields are intended to be within the scope of the following claims.

The invention claimed is:

1. A hanging drop array plate comprising:
a top surface and a bottom surface, said top surface bounded by one or more edges,
a plurality of holes, each said hole extending from an opening in said top surface to an outlet at said bottom surface, said plurality of holes configured to accommodate a corresponding plurality of hanging drops formed by application of a liquid through said opening of each of said holes, wherein a single drop hangs from a respective one of each of said holes and distends under the influence of gravity beneath said outlet thereof to enable the culturing of cells therein,
said bottom surface including a plateau feature surrounding each of said holes, said plateau feature configured to restrain a hanging drop to a confined region about the respective said hole; and
said top surface including an upper reservoir configured to receive a body of liquid restricted from said plurality of holes for maintaining a substantially stable humidity above said plurality of holes, said upper reservoir disposed along one or more of said edges of said top surface.

2. The array plate of claim 1, wherein said upper reservoir substantially surrounds said plurality of holes.

3. The array plate of claim 1, wherein said top surface includes a peripheral rim disposed adjacent said one or more edges of said top surface, said peripheral rim having a rim height measured perpendicularly from said top surface.

4. The array plate of claim 3, further including a wall structure, said wall structure surrounded by said peripheral rim and inset therefrom with said upper reservoir formed in a space therebetween, said wall structure having a wall height measured perpendicularly from said top surface, said wall height being shorter than said rim height.

5. The array plate of claim 1, wherein each said hole is approximately 1.6 mm in diameter.

6. The array plate of claim 1, further including a tray configured to form an enclosed space below said bottom surface in spaced relation therefrom so as to maintain separation from the hanging drops.

7. The array plate of claim 6, wherein said tray includes at least one lower reservoir configured to receive a body of liquid for maintaining a substantially stable humidity below said plurality of holes.

8. The array plate of claim 7, wherein said tray is fabricated from an optically transparent material.

9. The array plate of claim 1, wherein said plateau comprises an annular ring structure.

10. A method of cell analysis, comprising:
   a) inserting a plurality of hanging drops into the hanging drop array plate of claim 1; and
   b) performing on one or more of the hanging drops an analysis method selected from the group consisting of cell culturing, cell maintaining, cell analysis, cell testing, and combinations thereof.

* * * * *